US012324699B2

United States Patent
Venkatraman et al.

(10) Patent No.: US 12,324,699 B2
(45) Date of Patent: Jun. 10, 2025

(54) SYSTEMS AND METHODS FOR ELECTRONIC STETHOSCOPE WIRELESS AUSCULTATION

(71) Applicant: Eko Health, Inc., Emeryville, CA (US)

(72) Inventors: Subramaniam Venkatraman, Oakland, CA (US); Dan Freschl, Oakland, CA (US); Connor Landgraf, Oakland, CA (US); Michael Thompson, San Francisco, CA (US); Niladri Bora, Grass Valley, CA (US)

(73) Assignee: EKO HEALTH, INC., Emeryville, CA (US)

( * ) Notice: Subject to any disclaimer, the term of this patent is extended or adjusted under 35 U.S.C. 154(b) by 877 days.

(21) Appl. No.: 17/313,842

(22) Filed: May 6, 2021

(65) Prior Publication Data

US 2022/0354451 A1     Nov. 10, 2022

(51) Int. Cl.
*A61B 7/04*     (2006.01)
*A61B 5/00*     (2006.01)
*H04R 1/10*     (2006.01)

(52) U.S. Cl.
CPC ............ *A61B 7/045* (2013.01); *A61B 5/0004* (2013.01); *A61B 5/7264* (2013.01); *A61B 5/7475* (2013.01); *A61B 7/04* (2013.01); *H04R 1/10* (2013.01); *H04R 2420/07* (2013.01)

(58) Field of Classification Search
CPC .. A61B 7/04; A61B 7/045; A61B 7/02; H04R 1/10; H04R 1/46; H04R 2420/07
USPC ............................................ 381/67; 181/131
See application file for complete search history.

(56) References Cited

U.S. PATENT DOCUMENTS

| | | | | |
|---|---|---|---|---|
| 2008/0232605 A1* | 9/2008 | Bagha | ...................... | A61B 7/04 381/67 |
| 2013/0223646 A1* | 8/2013 | Lee | .......................... | H04R 3/02 381/94.5 |
| 2014/0056433 A1* | 2/2014 | Emerson, III | ........ | G06F 16/634 381/56 |

(Continued)

FOREIGN PATENT DOCUMENTS

| | | | | |
|---|---|---|---|---|
| CN | 107550515 A | | 1/2018 | |
| CN | 208591059 U | * | 3/2019 | ............... A61B 7/04 |

(Continued)

OTHER PUBLICATIONS

Great Britain Intellectual Property Office, Search Report under Section 17(5) Issued in Application No. GB2203107.4, Sep. 6, 2022, 5 pages.

(Continued)

*Primary Examiner* — Ahmad F. Matar
*Assistant Examiner* — Sabrina Diaz
(74) *Attorney, Agent, or Firm* — McCoy Russell LLP

(57) ABSTRACT

The present description relates generally to methods and systems for wireless communication between a digital (e.g., electronic) stethoscope and other electronic devices (e.g., computing and listening devices). In one example, a method comprises operating an electronic stethoscope in one of an internal digital mode and a wireless digital mode based on a detected user action. In this way, the electronic stethoscope may be quickly adjusted between projecting sound via integrated speakers and transmitting sound to an external electronic device, enabling efficient remote monitoring of a patient.

10 Claims, 9 Drawing Sheets

(56) References Cited

U.S. PATENT DOCUMENTS

2016/0262717 A1* 9/2016 Smith .................. A61B 5/0022
2020/0205770 A1   7/2020 Friedman et al.
2021/0345890 A1* 11/2021 Dey ...................... A61B 5/087

FOREIGN PATENT DOCUMENTS

| CN | 111493926 A | 8/2020 | | |
|----|----|----|----|----|
| CN | 111700637 A | 9/2020 | | |
| CN | 214387499 U | 10/2021 | | |
| CN | 113712588 A | 11/2021 | | |
| JP | 2015006232 A | 1/2015 | | |
| KR | 20170067950 A | 6/2017 | | |
| WO | WO-2018098716 A1 * | 6/2018 | ............. | G06F 19/34 |
| WO | 2021061754 A1 | 4/2021 | | |

OTHER PUBLICATIONS

"Bluetooth Hearing Aids Are Ready for Prime Time," Bluetooth Website, Available Online at https://www.bluetooth.com/blog/bluetooth-hearing-aids-are-ready-for-prime-time/, Feb. 25, 2020, 4 pages.

"How to Use Bluetooth Stethoscopes for Wireless Auscultation," Eko Health Website, Available Online at https://www.ekohealth.com/solution/learning/how-to-use-bluetooth-sthethoscopes-for-wireless-auscultation, Retrieved On Aug. 5, 2021, 12 pages.

"Precision Care, Anywhere," Eko Health Website, Available Online at https://www.ekohealth.com/solution/telemedicine, Retrieved On Aug. 5, 2021, 7 pages.

* cited by examiner

SYSTEMS AND METHODS FOR ELECTRONIC STETHOSCOPE WIRELESS AUSCULTATION

FIELD

The present description relates generally to methods and systems for wireless communication between a digital stethoscope and other electronic devices.

BACKGROUND/SUMMARY

Auscultation, the process of listening to internal sounds of a body, has historically been performed with an acoustic stethoscope. As one example, the acoustic stethoscope may include a two-sided chestpiece attached to hollow tubing that branches to two separate earpieces. A diaphragm on one side of the chestpiece may transmit high frequency sounds to the earpieces, or a bell on the other side of the chestpiece may transmit low frequency sounds to the earpieces. However, such acoustic stethoscopes are unable to digitize sounds that can be easily analyzed and shared electronically.

In contrast, an electronic (e.g., digital) stethoscope may generate digital audio data via an electronic chestpiece that may include components for noise amplification, digital display, sound recording, and wireless signal transmission. For example, the electronic stethoscope may wirelessly transmit audio data to a listening device (e.g., a pair of headphones or hearing aids) or a computing device (e.g., a smartphone or laptop computer) via a wireless connection, such as a Bluetooth® connection.

However, the inventors herein have recognized potential issues with existing electronic stethoscope systems. As one example, it may be desirable to have multiple listeners or multiple connections to the electronic stethoscope, which a single Bluetooth connection does not allow. Additionally, it may be advantageous to allow the electronic stethoscope to wirelessly connect to one or more electronic devices, including computing devices and listening devices, automatically when wireless auscultation is desired. As another example, it may be desirable to have a patient place the electronic stethoscope instead of a clinician in order to reduce physical contact between the patient and the clinician. This may be particularly desirable when the patient is suspected of being exposed to an infectious disease, for example.

In one example, the issues described above may be addressed by a method, comprising: operating an electronic stethoscope in one of an internal digital mode and a wireless digital mode based on a detected user action. In this way, an internal speaker may be shut off when earpieces are not connected to the electronic stethoscope, such as when only an external listening device is used to listen to physiological noises recorded by the electronic stethoscope, and the electronic stethoscope may be operated wirelessly.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1A:
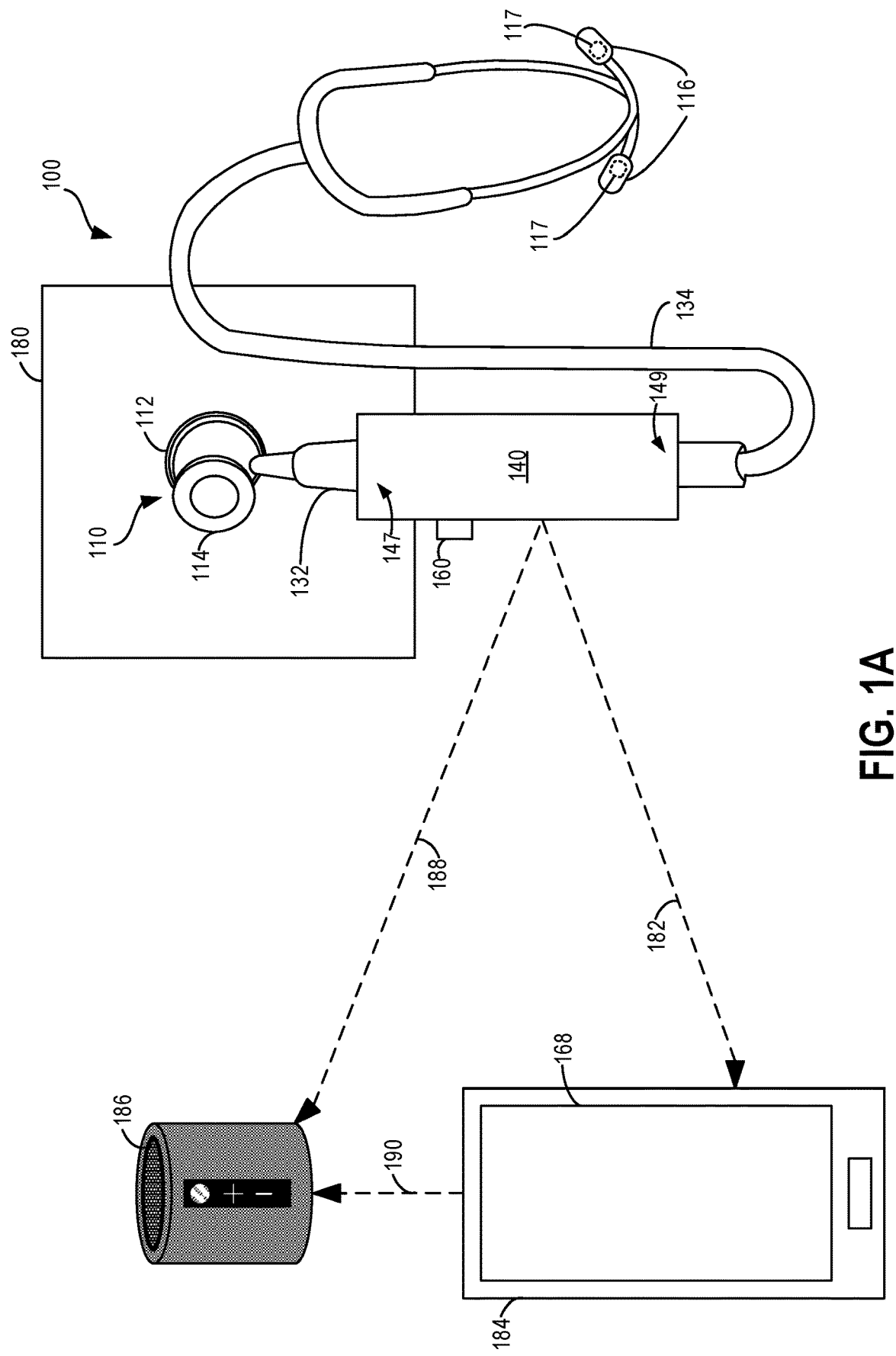
FIG. 1A is a schematic drawing showing a stethoscope with an electronic stethoscope device in a first mechanical configuration, with earpieces mechanically and acoustically connected to the electronic stethoscope device.
Figure 2:
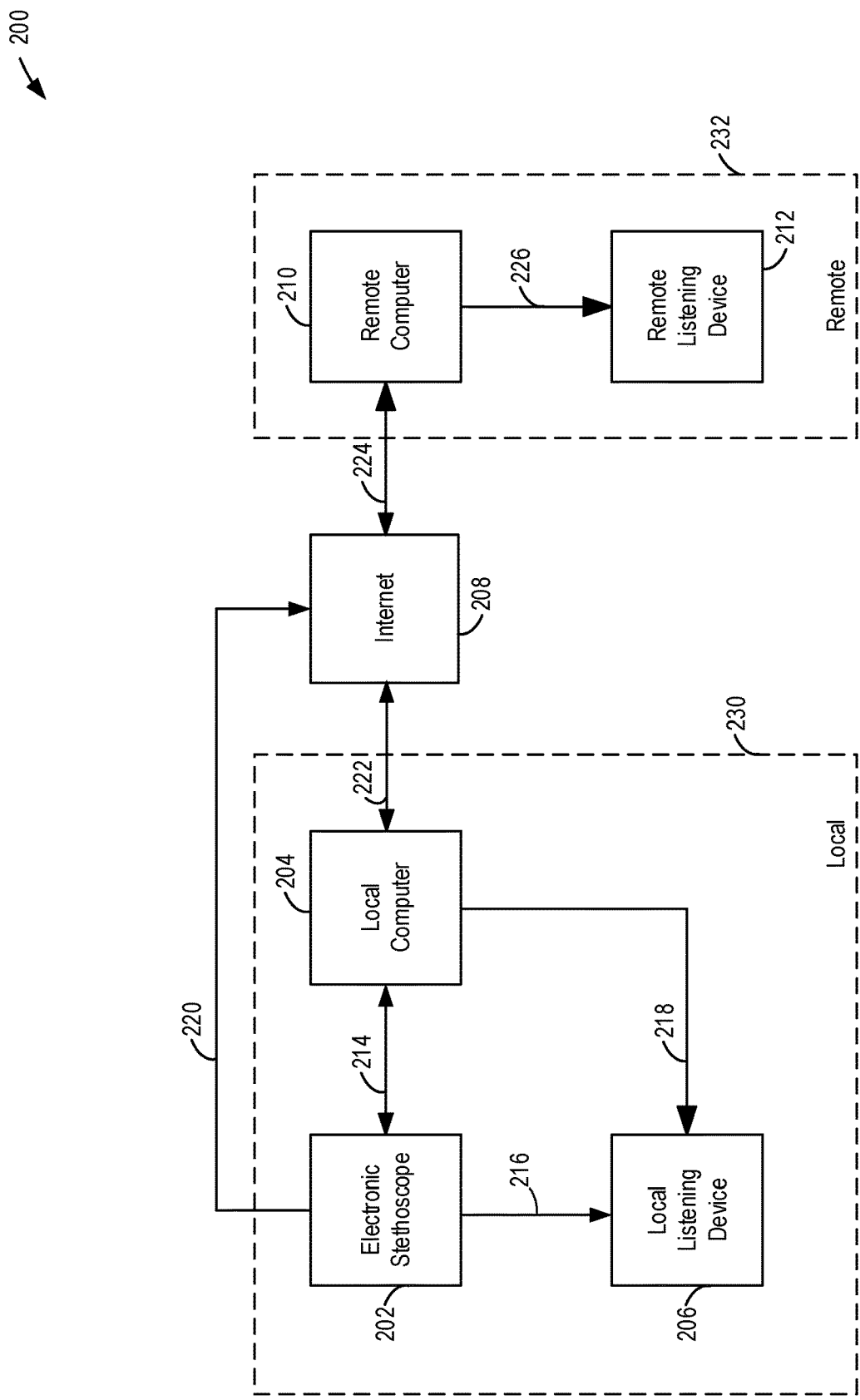
FIG. 2 shows a block diagram of the electronic stethoscope device in communication with other electronic devices.
Figure 3:
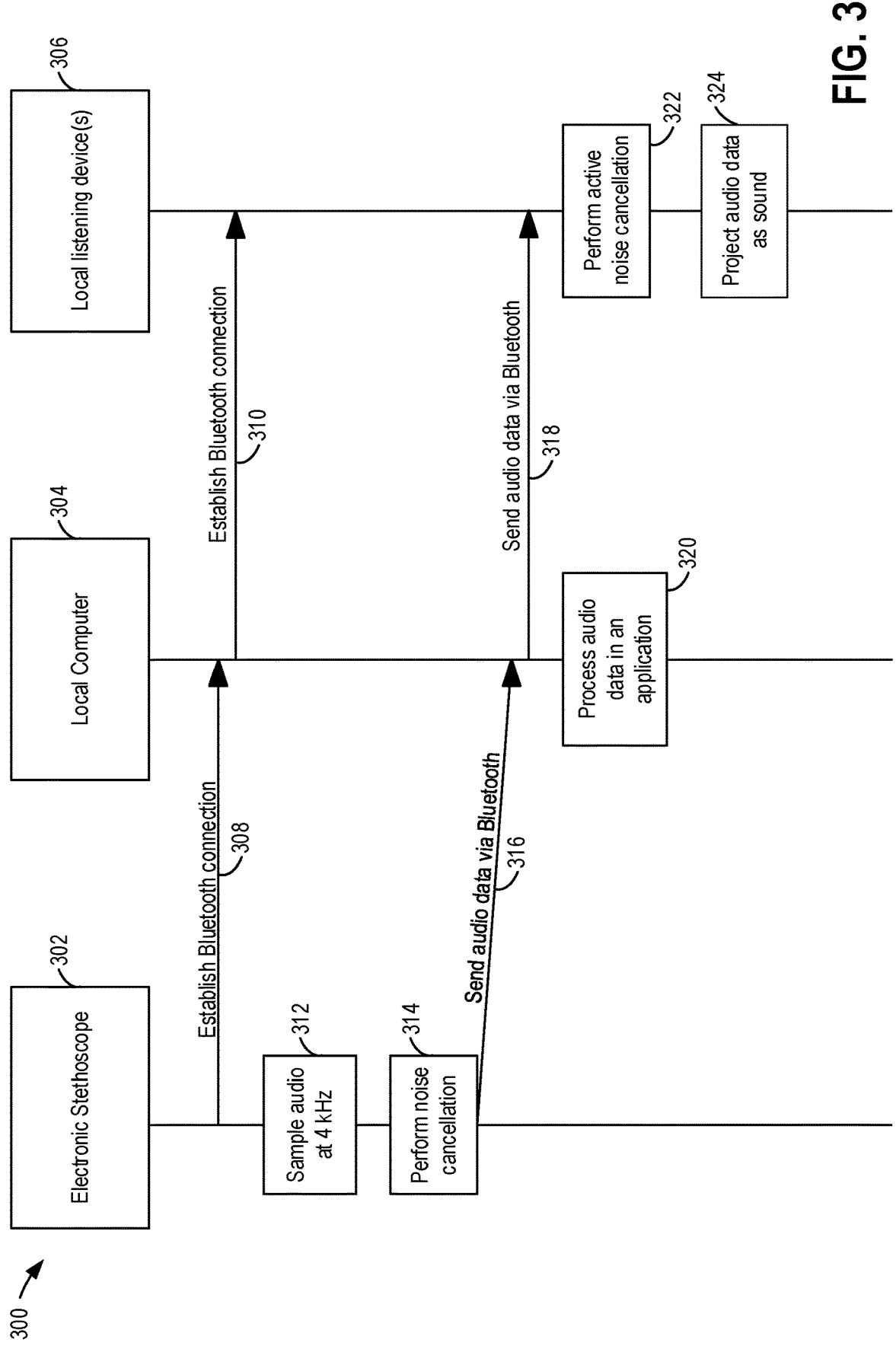
FIG. 3 shows an example communication diagram for data exchanged between the electronic stethoscope, a local computer, and local listening device(s).
Figure 4:
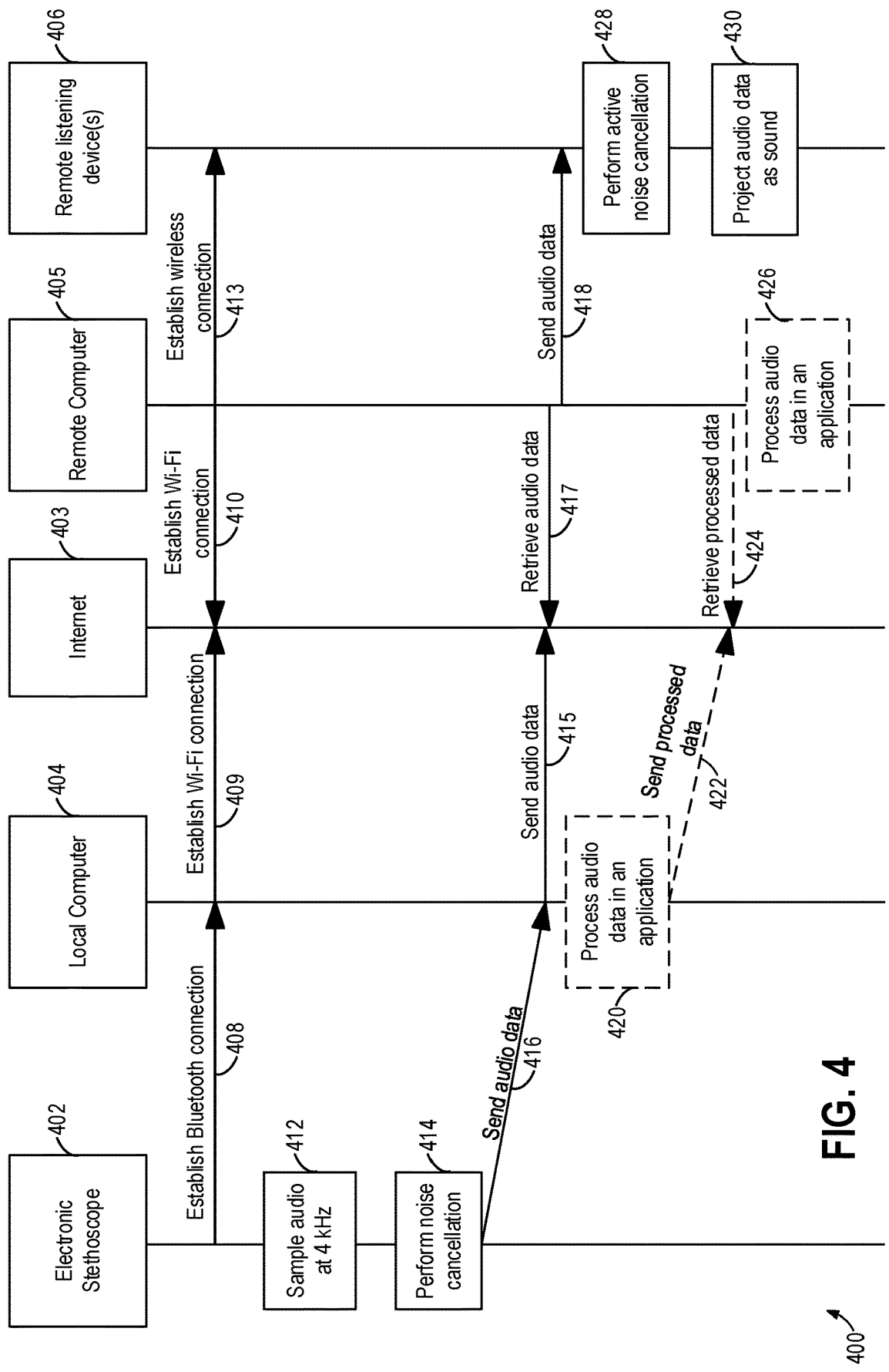
FIG. 4 shows an example communication diagram for data exchanged between the electronic stethoscope, a local computer, a network, a remote computer, and remote listening device(s).
Figure 5:
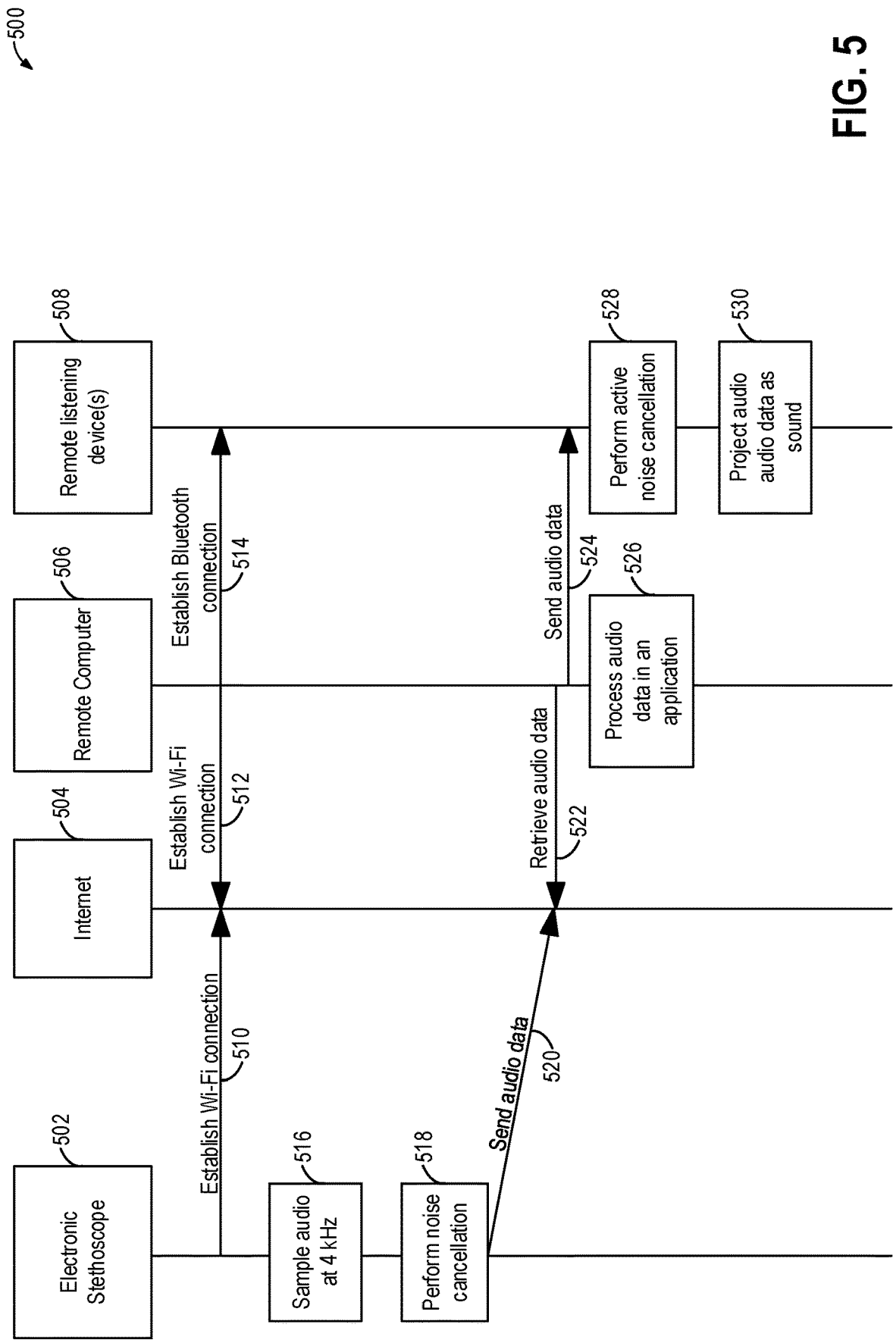
FIG. 5 shows an example communication diagram for data exchanged between the electronic stethoscope, a network, a remote computer, and remote listening device(s).

The present description relates generally to methods and systems for wireless communication between a digital stethoscope and other electronic devices. For example, the digital (e.g., electronic) stethoscope may be the electronic stethoscope shown in FIGS. 1A-1C having the electronic stethoscope device particularly shown in FIG. 1B that contains electrical components of the electronic stethoscope, including components for processing and wirelessly transmitting audio data. FIG. 1A shows a first configuration of the electronic stethoscope with an output tubing and earpieces attached, while FIG. 1C shows a second configuration of the electronic stethoscope without the output tubing and earpieces attached. FIG. 2 schematically shows a high-level communication architecture for how the electronic stethoscope may communicate with local and/or remote computing devices and listening devices. FIGS. 3-5 depict communication diagrams showing specific examples of connections and data sharing between the electronic stethoscope and other devices (e.g., local and/or remote computing devices and listening devices). For example, FIG. 3 shows the electronic stethoscope creating a Bluetooth connection with a computing device, and the computing device connects to a listening device through another Bluetooth connection. As another example, FIG. 4 shows the electronic stethoscope creating a Bluetooth connection to a local computing device, which then connects to a remote computing device via a network. As a further example, FIG. 5 shows the electronic stethoscope directly connecting to the network to transmit audio data to the remote computing device. The electronic stethoscope may establish one or more wireless connections to external device(s) (e.g., local and/or remote computing devices and listening devices), generate the audio data, and wireless transmit the audio data to the external device(s) according to the methods shown in FIGS. 6 and 7, for example.

Figure 1B:
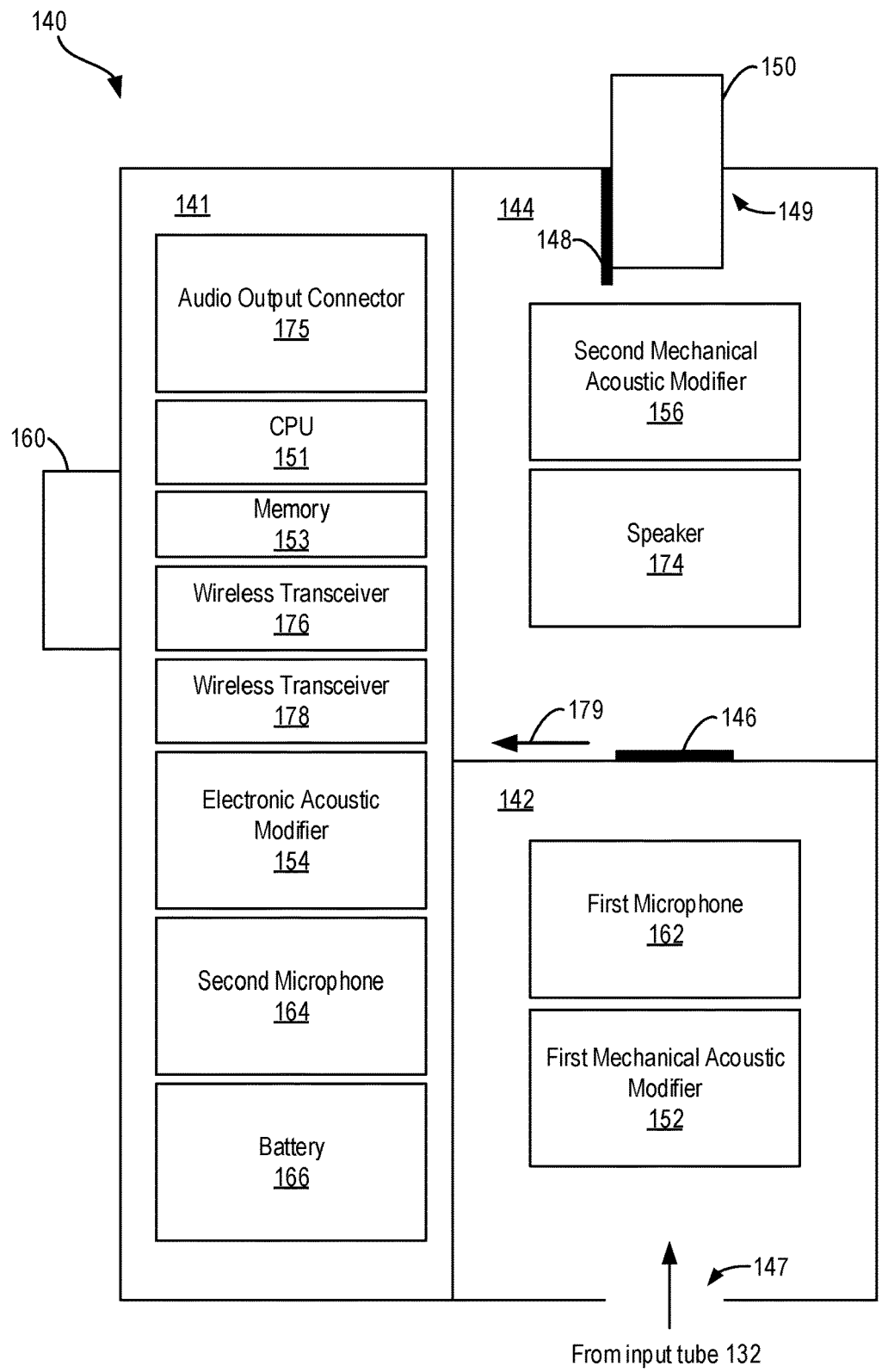
FIG. 1B is a block diagram showing the components of the electronic stethoscope device shown in FIG. 1A.
Figure 1C:
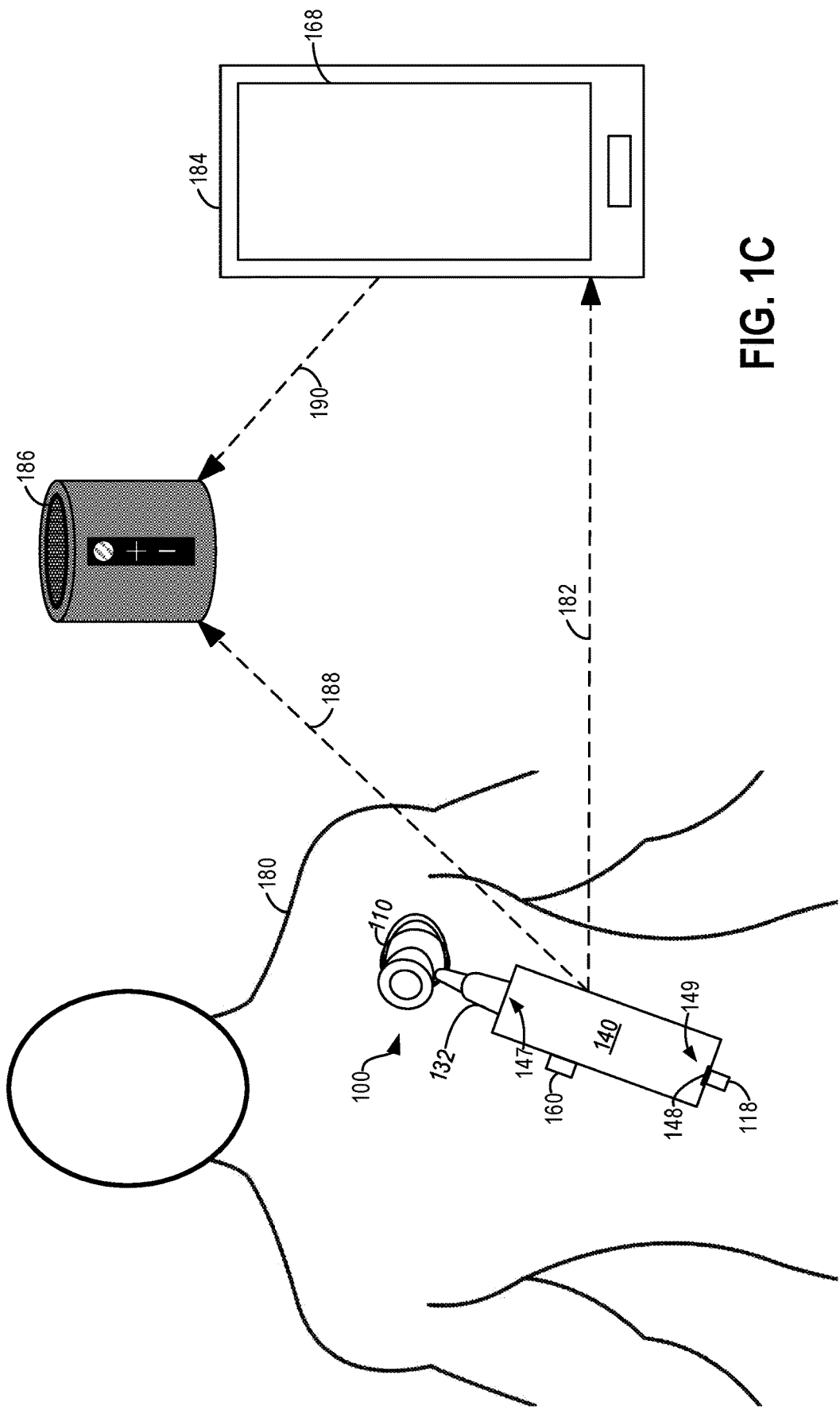
FIG. 1C schematically shows the electronic stethoscope in a second mechanical configuration, without the earpieces mechanically and acoustically connected to the electronic stethoscope device.

Turning now to the figures, FIGS. 1A-1C show an electronic stethoscope 100. Referring first to FIG. 1A, the electronic stethoscope 100 is shown in a first mechanical configuration. The electronic stethoscope 100 includes a chestpiece 110, an input tube 132, an electronic stethoscope device 140, and an output tube 134. The chestpiece 110 is in acoustic communication with an input 147 of the electronic stethoscope device 140 through the input tube 132. The electronic stethoscope device 140 is in acoustic communication with earpieces 116 through the output tube 134 at an output 149 of the electronic stethoscope device 140.

The chestpiece 110 may include a diaphragm 112, which is a sealed membrane with air inside that vibrates from external noises. The diaphragm 112 moves a column of air inside the input tube 132 according to the vibrations caused by the external noises, which in turn creates sounds that may be transmitted through the input tube 132 to the electronic stethoscope device 140. In some examples, the chestpiece 110 may include a bell 114 in addition to the diaphragm 112. The bell 114 may be an open hollow cup or may include a smaller sealed membrane than the diaphragm 112, and air inside the bell 114 may vibrate from external noises to produce acoustic pressure waves that may transmitted through the input tube 132. The diaphragm 112 may be used for higher frequency auscultation, such as heart beats and breath sounds, while the bell 114 may be used for lower frequency auscultation, such as heart murmurs and bowel sounds. The chestpiece 110 may be placed on a patient (e.g., subject) 180 by the patient 180 or by a clinician (not shown) for auscultation. The clinician or the patient 180 may listen to bodily sounds produced by the patient through the earpieces 116.

In some examples, the earpieces 116 may include speakers 117 positioned therein. When included, the speakers 117 may be in electronic communication with the electronic stethoscope device 140 when the output tube 134 is coupled to the output 149 of the electronic stethoscope device 140. Further, the speakers 117 may be automatically powered on when the electronic stethoscope 100 is operated in an internal (e.g., wired) digital mode and automatically powered off when the electronic stethoscope 100 is operated in a wireless digital mode, as will be elaborated herein with respect to FIGS. 1B and 6.

The electronic stethoscope device 140 may connect to other electronic devices through wireless connections. For example, the electronic stethoscope device 140 may connect to an external computing device 184 through a first wireless connection 182, which types of connections will be elaborated below. The external computing device 184 may be a mobile device, such as a smartphone, a tablet, a smartwatch, a laptop computer, or a personal digital assistant (PDA), for example. Alternatively, the external computing device 184 may be a stationary device, such as a desktop computer or server. In still other examples, the external computing device 184 may be included in a computing network, such as a cloud computing network. The external computing device 184 may include a processor operatively connected to memory (such as random-access memory, read-only memory, flash memory, a hard disk, etc.) as well as a communications interface for sending/receiving wired or wireless signals from a network and/or other computing devices, including the electronic stethoscope device 140. Further, the external computing device 184 includes a user interface 168, such as a display for outputting information to a user and one or more of a touchscreen, a trackball, hard keys/buttons, a keyboard, a mouse, and a trackpad for receiving user inputs. The external computing device 184 may operate a software application that receives the user inputs via the user interface 168 to adjust operation of the electronic stethoscope device 140. Upon initiation by the user, the software application may run in a background mode that facilitates an automatic connection of the external computing device 184 to the electronic stethoscope device 140 while reducing power consumption, as will be elaborated below with respect to FIG. 7. By connecting wirelessly to the external computing device 184, the electronic stethoscope device 140 may send audio data and analysis of the audio data to the external computing device 184.

As another example, the electronic stethoscope device 140 may connect to an external listening device 186 through a second wireless connection 188, and sounds recorded by the electronic stethoscope device 140 may be projected by the external listening device 186 for the patient 180 or the clinician to hear. The external listening device 186 may be a speaker, headphones, earbuds, hearing aids, or another device capable of projecting sound and forming wireless connections to other devices. In some examples, the external computing device 184 may connect to the external listening device 186 through a third wireless connection 190 instead of the electronic stethoscope device 140 connecting directly to the external listening device 186. In such examples, recorded sounds may be sent from the electronic stethoscope device 140 to the external computing device 184 and from the external computing device 184 to the external listening device 186. Further configurations of different connections to various devices will be described in below with respect to FIGS. 2-5.

In some examples, a conventional, non-digital stethoscope may be modified to become the electronic stethoscope 100 by inserting the electronic stethoscope device 140 into its tubing (e.g., between the input tube and the output tube of the conventional stethoscope). As will be elaborated below with respect to FIG. 1B, the electronic stethoscope device 140 includes components for recording and sharing auscultations. However, in some examples, the electronic stethoscope 100 may be selectively operated in an acoustic mode, wherein electronic components within the electronic stethoscope device 140 are bypassed and/or switched "off," and sounds generated via the chestpiece 110 may be transmitted to the earpieces 116 without digital processing. Further, as will be described with respect to FIG. 1C, in some examples, the electronic stethoscope device 140 may be disconnected from the output tube 134 and the earpieces 116, and the acoustic mode may be disabled.

Continuing to FIG. 1B, in some examples, the electronic stethoscope device 140 includes a body 141 that houses internal components, examples of which are elaborated below, and an airway with two chambers therein. The electronic stethoscope device 140 includes a first chamber 142 proximate to the input 147 and a second chamber 144 proximate to the output 149, both of which are configured to transmit acoustic signals. A switching valve 146 is positioned between the first chamber 142 and the second chamber 144. When the switching valve 146 is open, acoustic signals can be transmitted between the first chamber 142 and the second chamber 144, and the electronic stethoscope 100 is said to be in an acoustic mode of operation. When the switching valve 146 is closed, the transmission of acoustic signals between the first chamber 142 and the second chamber 144 is blocked, and the electronic stethoscope is said to be in a digital mode of operation.

In some examples, the first chamber 142 includes a first mechanical acoustic modifier 152 positioned therein. Further, in some examples, the first chamber 142 additionally or alternatively includes a first microphone 162 positioned therein. The first mechanical acoustic modifier 152 may include one or more mechanical acoustic filters. Example mechanical acoustic filters include, but are not limited to, vent holes whose size and shape are configured to filter specific frequency(ies), mass damper systems to compensate for acoustic overload, chamber shapes and sizes that enhance acoustic resonance, foam mechanical filters that dampen certain frequencies, and chamber shapes and sizes that reduce (e.g., minimize) impedance mismatches between the input tube 132 and/or the output tube 134 and the listener's ear.

Thus, the first mechanical acoustic modifier 152 may include one or more of the mechanical acoustic filters or any combination of the mechanical acoustic filters discussed above. When the first mechanical acoustic modifier 152 is included in the first chamber 142, it is positioned between the input 147, which comprises an opening in the body 141 to the input tube 132, and the first microphone 162. Due to the positioning of the first mechanical acoustic modifier 152, the auscultated sound picked up by the chestpiece 110 (shown in FIG. 1A) is modified by the first mechanical acoustic modifier 152 before being detected by the first microphone 162, which converts the auscultated sound into an auscultated electronic signal. In this way, the first mechanical acoustic modifier 152 may reduce unwanted sound frequencies and increase an output of desired sound frequencies in the auscultated electronic signal. However, when there is no first mechanical acoustic modifier 152 in the first chamber 142, the first microphone 162 may directly detect auscultated sound picked up by the chestpiece 110 and convert the unmodified auscultated sound into the auscultated electronic signal.

The electronic stethoscope device 140 includes a computer processing unit (CPU) 151, such as a microcontroller unit (MCU), positioned within the body 141. The CPU 151 receives inputs and/or sends outputs to various electronic components, including the first microphone 162 and additional electronic components of the electronic stethoscope device 140 that will be described further herein. In some examples, there is one microdevice that contains the CPU 151 and some or all of the electronic and electrical components. In some arrangements, the CPU 151 and the electronic and electrical components are positioned on two or more microdevices. The CPU 151 is operatively coupled to a memory 153, which includes one or more of a non-transitory (e.g., read-only) memory, a keep alive memory, and a random-access memory. For example, the CPU 151 is configured to access and execute instructions stored in the memory 153 according to one or more routines, an example of which will be described below with respect to FIG. 6.

The electronic stethoscope device 140 includes an electronic acoustic modifier 154 in the electronic stethoscope device 140 and in electrical communication with the CPU 151. In some examples, the electronic acoustic modifier 154 is a stand-alone device. In other examples, the electronic acoustic modifier 154 is firmware within the CPU 151. The electronic acoustic modifier 154 is configured to receive the auscultated electronic signal from the first microphone 162, modify the auscultated electronic signal to form a modified electronic signal, and transmit the modified electronic signal to the speakers 117 internal to the earpieces 116 or a speaker (or electroacoustic transducer) 174 internal to the body 141.

In some examples, the CPU 151 analyzes the auscultated electronic signal or on the modified electronic signal to extract information about the condition of a patient being evaluated with the electronic stethoscope or to suggest a preliminary diagnosis. Additionally or alternatively, the analysis may be performed via a computing device or system that is communicatively connected to the electronic stethoscope device 140, such as the external computing device 184 shown in FIGS. 1A and 1C or a cloud-based system. For example, an analysis algorithm stored in the memory 153 or accessed via the software application on the external computing device 184 may evaluate the audio data recorded by the first microphone 162 to detect a presence or absence of heart murmurs. In some examples, the CPU 151 can amplify the modified electronic signal before it is transmitted to the speaker 174.

In some examples, the speaker (or electroacoustic transducer) 174 is positioned in the second chamber 144. The speaker 174 is configured to produce no sound when the electronic stethoscope is operated in the acoustic mode of operation (e.g., when the switching valve 146 is open). As another example, the speaker 174 may not produce sound when output tube 134 shown in FIG. 1A is disconnected from the output 149, such as shown in FIG. 1C and elaborated below. The speaker 174 is configured to receive the modified electronic signal from the electronic acoustic modifier 154 and to convert the modified electronic signal to modified sound for transmission to the output tube 134 when the electronic stethoscope device 140 is in the digital mode of operation (e.g., when the switching valve 146 is closed) and the output tube 134 is connected to the output 149. In some examples, the speaker 174 is a piezo-based speaker or an acoustic resonator speaker. In some examples the speaker 174 is configured to amplify the modified sound so it is louder than the original auscultated sound. For example, the speaker 174 may amplify the modified sound alone or in conjunction with the electronic acoustic modifier 154.

During the digital mode of operation when the output tube 134 is attached (e.g., the wired digital mode of operation), the modified sound output from the speaker 174 passes through an output portion of the airway between the switching valve 146 and the output tube 134 before it is transmitted to the earpieces 116 (e.g., shown in FIG. 1A) via the output tube 134. The speaker 174 and the airway may be positioned within the electronic stethoscope device 140 such that the modified sound output from the speaker 174 does not couple to a second microphone 164 that senses noise from the environment. For example, the second microphone 164 may face an external environment of the electronic stethoscope device 140 and may be configured to detect noise and to convert the noise into an electronic noise signal, as will be elaborated below.

The electronic stethoscope device 140 includes an optional audio output connector 175, such as a headphone jack or USB-type port, which can receive the modified electronic signal from the electronic acoustic modifier 154. A user may physically connect a peripheral device to the audio output connector 175. Examples of such peripheral devices include but are not limited to a computer, a cell phone, and a listening device configured to convert the modified electronic signal to sound.

In some examples, a first wireless transceiver 176 is positioned in the electronic stethoscope device 140, such as within the body 141, as shown, or, in other embodiments, within either the first chamber 142 or the second chamber 144. In some examples, the first wireless transceiver 176 may be included in a circuit board, such as a printed circuit board (PCB), that may also include one or more electronic components, such as the first microphone 162, the second microphone 164, and the CPU 151. The first wireless transceiver 176 is in electrical communication with the electronic acoustic modifier 154. The first wireless transceiver 176 is configured to receive the modified electronic signal from the electronic acoustic modifier 154, convert the modified electronic signal to a modified wireless signal, and wirelessly transmit the modified wireless signal from the electronic stethoscope to an external listening device, such as the external listening device 186 shown in FIGS. 1A and 1C, and/or a peripheral device, such as external computing device 184 shown in FIGS. 1A and 1C. The first wireless transceiver 176 may use any appropriate communication types and protocol, such as television, cellular phone, Wi-Fi, satellite, two-way radio, infrared, short-range microwave signals, IEEE 802.11 compliant radio signals, Bluetooth®, or Low Energy Bluetooth (BLE). In some examples, the first wireless transceiver 176 may be configured to pair directly to the external listening device 186 and/or the external computing device 184. Alternatively, the first wireless transceiver 176 may communicate data to the external listening device 186 and/or the external computing device 184 through an intermediary device, such as a wireless router maintaining a local area network (WLAN) or through a connection to the internet. The first wireless transceiver 176 may also be configured to receive signals from one or more peripheral devices, including the external computing device 184 shown in FIGS. 1A and 1C. In some examples, the first wireless transceiver 176 is in electrical communication with the first microphone 162, and can wirelessly transmit the auscultated electronic signal to the external listening device 186 and/or the external computing device 184.

The electronic stethoscope device 140 may further include at least one additional wireless transceiver, including a second wireless transceiver 178 shown in FIG. 1B. The second wireless transceiver 178 may operate as described above with respect to the first wireless transceiver 176. As such, the first wireless transceiver 176 and the second wireless transceiver 178 enable the electronic stethoscope device 140 to form two separate wireless connections with external devices. For example, the first wireless transceiver 176 may connect to the external computing device 184 shown in FIGS. 1A and 1C while the second wireless transceiver 178 connects to the external listening device 186 shown in FIGS. 1A and 1C. As another example, the first wireless transceiver 176 may connect to a first external computing device while second wireless transceiver 178 connects to a second external computing device. As still another example, the first wireless transceiver 176 may connect to a first external listening device while second wireless transceiver 178 connects to a second external listening device.

It may be understood that sound may be projected by the speaker 174 and transmitted through the output tube 134 to the earpieces 116 (or alternatively, projected via the speakers 117 positioned in the earpieces 116) and also transmitted via the first wireless transceiver 176 at the same time. For example, a user (e.g., a clinician or the patient 180) may listen to physiological sounds while placing the electronic stethoscope on the patient 180 via the earpieces 116 while one or more remote clinicians listen simultaneously via the external listening device 186.

As described above, the auscultated electronic signal or the modified electronic signal may be analyzed on the electronic stethoscope device 140 by the CPU 151. In some examples, the auscultated electronic signal or the modified electronic signal may be transmitted by the first wireless transceiver 176 or through the audio output connector 175 to the external listening device 186 and/or the external computing device 184. Such signals can then be analyzed on the external computing device 184 to extract information about the condition of the patient or to suggest the preliminary diagnosis. The results of such an analysis can be transmitted back to the first wireless transceiver 176 and can be communicated to a user of the electronic stethoscope device 140 visually or with sound. Visual information can be provided using light emitting diodes (LEDs) or other light sources or displays (not shown) on the electronic stethoscope device 140. Sound may be in the form of beeps, tones, or voice transmitted through the speaker 174 or the external listening device 186 (not shown in FIG. 1B). The external listening device 186 may be wireless headphones, a hearing aid, or a wireless speaker, for example, that is not included within the electronic stethoscope 100.

In some examples, a second mechanical acoustic modifier 156 is positioned near the output 149 of the electronic stethoscope device 140 where it joins the output tube 134. Similar to the first mechanical acoustic modifier 152, the second mechanical acoustic modifier 156 may be a mechanical acoustic filter. The second mechanical acoustic modifier 156 may include one or more of the mechanical acoustic filters or any combination of the mechanical acoustic filters discussed above. Acoustic signals from the speaker 174 pass through the second mechanical acoustic modifier 156 before traveling through the output tube 134. The second mechanical acoustic modifier 156 further filters out unwanted sound frequencies and works in concert with processing performed by the electronic acoustic modifier 154 to increase auscultation sound output clarity and specificity.

The electronic stethoscope device 140 includes the second microphone 164 facing the external environment. The second microphone 164 is configured to detect noise from the external environment and to convert the noise into an electronic noise signal. In some examples, one or both of the first microphone 162 and the second microphone 164 is a micro-electrical-mechanical system (MEMS) microphone, an electret microphone, or a piezoelectric microphone. When such a second microphone 164 is included in the electronic stethoscope device 140, the electronic acoustic modifier 154 is configured to receive the electronic noise signal from the second microphone 164 and to use the electronic noise signal, for example, as part of active noise cancellation, in modifying the auscultated electronic signal to form the modified electronic signal. The second microphone 164 may sense noise from the environment via a port that fluidly couples with the environment. The second microphone and the port to the second microphone may be positioned such that they are mechanically isolated from the airway, the speaker 174, and the first microphone 162. The mechanical isolation of the second microphone reduces coupling of the auscultation sounds that are present within the airway, transmitted to the first microphone 162, and/or output from the speaker 174. As a result, unwanted feedback of auscultation sounds is reduced, noise cancellation processing is increased, and auscultation sound output clarity and specificity is increased.

Further, in some examples, local noise cancelling may be performed without use of the second microphone 164. For example, when an external speaker that is projected to the room (such as a public address system or loudspeaker) is used to broadcast the auscultation sound (e.g., the external listening device 186 shown in FIGS. 1A and 1C), the electronic stethoscope device 140 may utilize echo cancellation algorithms to remove the ambient sounds from the first microphone 162. For example, the echo cancellation algorithms may be stored in the memory 153 and may be executed by the CPU 151. Further, the echo cancellation algorithms may use knowledge of the sounds being broadcasted via the external speaker to remove the broadcasted sounds from the signal received from the first microphone 162. As a result, potential feedback or other acoustic artifacts that may confuse the listener and/or confound data processing algorithms may be reduced or eliminated.

Examples of the kinds of electronic signal modifications that may be performed using the electronic acoustic modifier 154 include, but are not limited to, active noise cancellation, single channel noise reduction (SCNR), and upward or downward expansion. In an exemplary embodiment of the active noise cancellation, the electronic acoustic modifier 154 receives the electronic noise signal from the second microphone 164 and reduces the amplitude of or removes the noise component from the auscultated electronic signal received from the first microphone 162, thus increasing a quality of the modified electronic signal. SCNR refers to techniques which may reduce the noise portion of the modified electronic signal through the use of temporal, spectral or statistical differences between the auscultated electronic signal and the electronic noise signal. A downward expander can reduce the gain on a signal when the amplitude of a signal is below a pre-set threshold. In some examples, the gain is reduced to zero. Any gain reduction may minimize noise detection when the chestpiece 110 is held against the air.

In some examples, the second microphone 164 can detect that the first microphone 162 is recording sounds from "open air," such as when the chestpiece 110 is held against the air, by comparing the signals coming from the two microphones. If the signals are highly correlated, the sounds that would otherwise be transmitted to the speaker 174 and/or the external listening device may be suppressed. This would prevent amplification of sounds when the chestpiece 110 is not on a patient and could prevent accidental exposure to undesirable amplified sounds from such things as sirens, speech, doors closing, etc. If the two microphones detect significantly different sounds, it is an indication that the chestpiece 110 may be on a surface intended to be auscultated, and amplification could be employed.

It should be understood that, in describing electrical communication, the phrase, "A is in electrical communication with B," describes both direct electrical communication from A and B or from B and A and also electrical communication that goes between A to B through the CPU 151, (e.g., from A to the CPU 151 to B and from B to the CPU 151 to A).

Electronic stethoscope device further includes a battery 166. The battery 166 may be a disposable battery or a rechargeable battery. If the battery 166 is a disposable battery, the outside of the electronic stethoscope device 140 may include a door (not shown) through which the battery 166 can be changed. If the battery 166 is a rechargeable battery, the outside of the electronic stethoscope device 140 may include a charging port (not shown) through which the battery 166 can be charged. Alternatively, the battery 166 may be charged wirelessly. The battery 166 is configured to supply power to the electronic components of the electronic stethoscope device 140, including, but not limited to, the first microphone 162, the electronic acoustic modifier 154, the second microphone 164, the speaker 174, the CPU 151, and the first wireless transceiver 176.

In some examples, the switching valve 146 acts also as an on/off switch for the electronic components of the electronic stethoscope device 140. When the switching valve 146 is open (acoustic mode), the electronic components are off (e.g., unpowered). When the switching valve 146 is closed (digital mode), the electronic components are on (e.g., powered). FIG. 1B shows the electronic stethoscope device 140 with the switching valve 146 in a closed position. When the switching valve 146 is in the closed position, an electrical connection is established for the various electronic components of the electronic stethoscope with a power source, such as the battery 166, which in turn results in current flow 179, thereby electrically powering the various electronic components, including the first microphone 162, the second microphone 164, the speaker 174, the first wireless transceiver 176, the CPU 151, the electronic acoustic modifier 154, and the audio output connector 175. In some embodiments, wherein one or more electronic components are arranged on the PCB, the circuit board may be electrically coupled to the switching valve 146 such that when the switching valve 146 is in the closed position during the digital mode of operation, the one or more electronic components on the circuit board may be electrically powered by the power source (e.g., the battery 166) via the switching valve 146.

When the switching valve 146 is in an open position (not shown), the electronic components of the electronic stethoscope device 140 are unpowered, and the electronic stethoscope 100 including the electronic stethoscope device 140 operates in the acoustic mode. During operation in the acoustic mode, the auscultation sound from the chestpiece 110 is transmitted to the input tube 132, and from the input tube 132 to the output tube 134 via the airway that is continuous from the first chamber 142 to the second chamber 144 via an opening of the switching valve 146. When the switching valve 146 is open, electrical connection between the various electronic components and the power source is not established, and as such modification of the auscultation sound obtained via the chestpiece 110 is performed via the first mechanical acoustic modifier 152 and/or the second mechanical acoustic modifier 156.

In some examples, the electronic stethoscope device 140 includes a user interface to receive user inputs, such as one or more of a power button or switch (not shown) with which a user may power on/activate the connection between the battery 166 and the electronic components (e.g., by closing switching valve 146) or power off/deactivate the connection between the battery 166 and the electronic components (e.g., by opening switching valve 146), a button or switch for establishing a wireless connection between the first wireless transceiver 176 and an outside receiver, a volume control (not shown) for the first microphone 162, and a volume control (not shown) for the second microphone 164. In the example shown, the electronic stethoscope device 140 includes a mode selection input 160, which may be a button or switch that allows the user to initiate wireless auscultation (e.g., operation in the wireless digital mode) by performing an action at the mode selection input 160. For example, the user may depress or toggle the mode selection input 160 to a first position to initiate wireless digital mode operation and depress or toggle the mode selection input 160 to a second, different position to initiate wired digital mode operation. Alternatively, wireless auscultation may be initiated via the user interface 168 of the external computing device 184 (shown in FIGS. 1A and 1C) or by disconnection of the output tube 134, such as will be elaborated below. Electronic stethoscope device 140 may also include one or more display outputs (not shown) positioned on an exterior of the electronic stethoscope device 140, such as indicator lights. In some examples, a display screen configured to show words or images may also be included as a display output. The indicator lights and/or the display screen may provide information about the state of the electronic stethoscope device 140 and/or provide information about the condition of the patient.

In some examples, the electronic stethoscope device 140 includes one or more devices to provide audio indicator signals (not shown) to provide sounds, such as beeps or verbal language, to indicate device operation status and/or information about the condition of the patient. In some examples, the volume of the audio indicator can be adjusted or turned off through user inputs.

In some examples, the body 141 of the electronic stethoscope device 140 may be connected to the output tube 134 shown in FIG. 1A via a connector 150 positioned at the output 149. The connector 150 may be a tapered hose barb, for example, or another type of coupler that enables the output tube 134 to be removably connected to the second chamber 144 at the output 149 and enables sound transmission. For example, the connector 150 may be hollow. Thus, the connector 150 may mechanically and acoustically couple the earpieces 116 to the electronic stethoscope device 140. The connector 150 may be integrated with (e.g., part of) the output tube 134 or may be a separate fitting. As shown, the connector 150 may be partially inserted into the second chamber 144, extending between the exterior of the electronic stethoscope device 140 and the interior of the electronic stethoscope device 140. However, other configurations are also possible. For example, the connector 150 may include an externally threaded portion shaped to mate with an internally threaded portion of the body 141.

The electronic stethoscope device 140 may further include a switch 148 positioned at the output 149 and in electronic communication with one or more electronic components of the electronic stethoscope device 140, such as the CPU 151. The switch 148 may be used to detect a mechanical configuration change of the electronic stethoscope 100. For example, the CPU 151 may actively detect whether or not the connector 150 is physically coupled to the body 141 based on a position of the switch 148. For example, when the switch 148 is in a first, open position shown in FIG. 1B, the CPU 151 may determine that the connector 150 (and therefore, the output tube 134 shown in FIG. 1A) is connected to the body 141 at the output 149. Conversely, when the switch 148 is in a second, closed position shown in FIG. 1C and elaborated below, the CPU 151 may determine that the connector 150 (and therefore, the output tube 134 shown in FIG. 1A) is not connected to (e.g., disconnected from) the body 141 at the output 149. In some examples, the CPU 151 may select an operating mode of the electronic stethoscope device 140 based on a detected position of the switch 148 in order to adjust operation of the speaker 174 (or the speakers 117 shown in FIG. 1A). The switch 148 may be an electromechanical switch, for example, that is mechanically actuated to the first, open position when the connector 150 is coupled to the electronic stethoscope device 140 and mechanically actuated to the second, closed position when the connector 150 is removed. As an example, when in the first position, the switch 148 may connect a circuit between the speaker 174 and the battery 166, whereas the circuit between the speaker 174 and the battery 166 may be broken when the switch 148 is in the second position. As such, the speaker 174 may be selectively powered (e.g., operated) while the connector 150 is coupled to the electronic stethoscope device 140 and the switch 148 is in the first position shown in FIG. 1B and not while the connector 150 is disconnected from the electronic stethoscope device 140 and the switch 148 is in the second position shown in FIG. 1C.

In other examples, different feedback signals may be used to determine whether or not the earpieces 116 are physically connected to the electronic stethoscope device 140. As one example, the CPU 151 may analyze signals from the first microphone 162 and/or a microphone positioned in the second chamber 144. As still another example, the CPU 151 may receive feedback from a component in the earpieces 116, such as a sensor and/or the speakers 117. For example, the sensor and/or the speakers 117 in the earpieces 116 may be selectively powered when the earpieces 116 are coupled to the body 141 via the connector 150, whereas electronic communication between the sensors and/or the speakers 117 and the electronic stethoscope device 140 is discontinued while the earpieces 116 are disconnected from the body 141. In still another example, a proximity sensor may be used to infer whether or not the earpieces 116 are connected based on a distance from the earpieces 116 from the electronic stethoscope device 140.

Continuing now to FIG. 1C, the electronic stethoscope 100 is shown in a second mechanical configuration, wherein the connector 150 shown in FIG. 1B and the output tube 134 shown in FIG. 1A are mechanically and acoustically disconnected from the electronic stethoscope device 140 and replaced with a cap 118 at the output 149. For example, the output tube 134 (and the connector 150) may be removed from the electronic stethoscope 100 and replaced with the cap 118 by a clinician (not shown) or the patient 180. The cap 118 and the input tube 132 may fully seal the electronic stethoscope device 140, rendering the electronic stethoscope device 140 waterproof. Although the cap 118 is shown in FIG. 1C as an external component that extends from the electronic stethoscope device 140, alternatively, the cap 118 may be an internal component of the electronic stethoscope device 140 that automatically covers the output 149 when the connector 150 is disconnected. For example, the cap 118 may be a spring-loaded component that slides or rotates to a (fully) closed position to fully seal the output 149 when the connector 150 shown in FIG. 1B is removed, whereas the cap 118 may be held in an open position when the connector 150 is attached to the electronic stethoscope device 140.

By replacing the output tube 134 of electronic stethoscope 100 with the cap 118, auscultation may be conducted wirelessly with more ease. For example, if the external listening device 186 is being used instead of earpieces 116 shown in FIG. 1A, the output tube 134 (and the connector 150 and the earpieces 116) may be removed to allow for ease of movement of electronic stethoscope 100 around and on a body of the patient 180. As described above, disconnecting the output tube 134 (e.g., via disconnecting the connector 150 shown in FIG. 1B) may automatically shut off the speaker 174 shown in FIG. 1B so that sound is no longer transmitted at the output. Further, the output tube 134 may be re-attachable, and reconnecting the output tube 134 to the output 149 of the electronic stethoscope device 140 may automatically activate the speaker 174 shown in FIG. 1B so that sound may be transmitted through the output tube 134, as also described above with respect to FIG. 1B.

In some embodiments, instead of or in addition to the cap 118, the electronic stethoscope 100 may be placed in a dedicated holder, such as a mounting rod that enables the user to place the electronic stethoscope from a greater distance than if holding the electronic stethoscope directly (e.g., similar to taking a picture using a "selfie stick"). In still other embodiments, the electronic stethoscope 100 may only include the chestpiece 110, the input tube 132, and the electronic stethoscope device 140. As such, the electronic stethoscope 100 may form an audio transducer that transmits data wirelessly and may not provide acoustic auscultation. Additionally, in some examples, the electronic stethoscope may have a smooth surface, easing the handling process of a user (e.g., patient 180 or clinician).

Turning now to FIG. 2, a block diagram of a communications network 200 between an electronic stethoscope 202 and external electronic devices is shown. For example, the electronic stethoscope 202 may be the electronic stethoscope 100 described with respect to FIGS. 1A-1C. As another example, the external electronic devices may include headphones, hearing aids, cellular phones (e.g., smartphones), desktop and/or laptop computers, and computing networks, examples of which will be described herein. Additionally, the communications network 200 may include both short-range communication technologies (e.g., Bluetooth) for connecting local devices and long-range communication technologies (e.g., Wi-Fi®) for connecting remote devices (e.g., through the internet), as will be elaborated below.

The electronic stethoscope 202 may connect to a local computer 204 positioned within a local area 230 through a first short-range connection 214. The local computer 204 may be desktop or laptop computer, cellular phone, tablet, wearable device (e.g., a smartwatch), or other computing device having a wireless transceiver. The first short-range connection 214 may be a radio signal with a relatively short range (e.g., a maximum distance within a range from 10 to 100 meters) that frequently (e.g., hundreds of times per second) changes channel frequency for security, such as Bluetooth. In some examples, the first short-range connection 214 may be a BLE connection. The BLE connection may use the same frequency band as traditional Bluetooth (e.g., 2.4 GHz) but may consume less power due to a lower data transmission rate, for example. Thus, the electronic stethoscope 202 and the local computer 204 may communicate with each other via the first short-range connection 214. Further, the local computer 204 may remotely control the electronic stethoscope 202. For example, a user may turn on and off active noise cancellation, filtering, and other electronic functions of the electronic stethoscope 202 via the local computer 204 without having to physically handle the electronic stethoscope 202.

The local area 230 may include a physical space around the electronic stethoscope 202 in which Bluetooth devices may connect and may range from approximately 10 meters to approximately 35 meters from the electronic stethoscope 202, depending on physical obstructions around the electronic stethoscope 202, receiver sensitivity, antenna gain, etc. Thus, in some examples, the local area 230 may be less than 10 meters around the electronic stethoscope 202 or more than 35 meters around the electronic stethoscope 202.

The local computer 204 may connect to a local listening device 206 through a second short-range connection 218, which may be a similar connection as the first short-range connection 214. As one example, the second short-range connection 218 may be a type of BLE audio transmission referred to as LE Audio. The local listening device 206 may include one or more hearing aids, headphones, and/or earbuds having a wireless transceiver, and the local listening device 206 may be used to project physiological sounds recorded by the electronic stethoscope 202. Additionally or alternatively, the electronic stethoscope 202 may connect directly with the local listening device 206 through a third short-range connection 216. For example, the electronic stethoscope 202 may connect to both the local listening device 206 and the local computer 204 through the two separate short-range connections, the third short-range connection 216 and the second short-range connection 218, respectively. For example, the electronic stethoscope 202 may include more than one Bluetooth radio to communicate with the local listening device 206 and the local computer 204 at the same time. In particular, BLE standards like BLE4.2 with data length extension and/or LE Audio may enable the third short-range connection 216 and the second short-range connection 218 to be simultaneously maintained without interference.

In some examples, the local computer 204 may connect to a second local listening device (not shown) using the second short-range connection 218 so that two distinct local listening devices may receive audio data generated by the electronic stethoscope 202. Alternatively, the electronic stethoscope 202 may connect directly with the local listening device 206 and the second local listening device through the third short-range connection 216 and the first short-range connection 214, respectively.

The electronic stethoscope 202 may connect to internet 208 (or other network) either directly or through the local computer 204. To connect to the internet 208 directly, the electronic stethoscope 202 may use a wireless transceiver (e.g., first wireless transceiver 176 shown in FIG. 1B) to connect to a first internet connection 220, which may then connect to a local router and modem (not shown) to connect to the internet 108. For example, the first internet connection 220 may be a Wi-Fi connection. Alternatively, the electronic stethoscope 202 may connect to the internet 208 through the local computer 204. As described above, the electronic stethoscope 202 may connect to the local computer 204 using the first short-range connection 214, and the local computer 204 may connect to the internet 208 through a second internet connection 222. The second internet connection 222 may be a wireless (e.g., Wi-Fi) connection to the router and modem, or the second internet connection 222 may be a wired connection to the local modem that connects to the internet 208, such as through an Ethernet cable.

Additionally or alternatively, the electronic stethoscope 202 may connect to remote devices through the internet 208. The remote devices reside in a remote area 232, which is a physical space covering everywhere outside of the local area 230. For example, if the local area 230 ends 35 meters from the electronic stethoscope 202, then the remote area 232 exists everywhere beyond the 35 meters. A remote computer 210 (e.g., a cellular phone, desktop computer, laptop, or other device with internet and Bluetooth connection abilities) may connect to the internet 208 through a third internet connection 224. The third internet connection 224 may be a wireless or wired connection to the internet, such as described above with respect to the second internet connection 222.

In some examples where the electronic stethoscope 202 is directly connected to the internet 208 through the first internet connection 220, the electronic stethoscope 202 may connect to the remote computer 210 through the internet 208. In this way, the electronic stethoscope 202 may connect to the remote computer 210 without the local computer 204 facilitating the connection between the electronic stethoscope 202 and the remote computer 210. However, in other examples, the electronic stethoscope 202 may not directly connect to the internet 208, and the electronic stethoscope 202 may instead connect to the remote computer 210 via the local computer 204. For example, the first short-range connection 214 may connect the electronic stethoscope 202 and the local computer 204, and the local computer 204 and the remote computer 210 may be connected to each other via the internet 208. Thus, the electronic stethoscope 202 may be connected to one or both of the local computer 204 and the remote computer 210 via various wireless communication protocols, examples of which will be elaborated below with respect to FIGS. 3-5.

The remote computer 210 may connect to a remote listening device 212. The remote listening device 212 include one or more earbuds, headphones, hearing aids, speakers, or other devices capable of projecting sound and connecting to other electronic devices wirelessly. The remote listening device 212 may connect to the remote computer 210 through a fourth short-range connection 226, which may be a Bluetooth (e.g., BLE or LE Audio) connection. Alternatively, the remote listening device 212 may connect to the remote computer 210 via a wired connection. The remote listening device 212 may be used to project sounds from audio data generated by and transmitted from the electronic stethoscope 202 so that a person within the remote area 232 may listen to physiological noises recorded by the electronic stethoscope 202.

Turning now to FIG. 3, a first example communication diagram 300 for data exchange between an electronic stethoscope 302, a local computer 304, and a local listening device(s) 306 is shown. For example, the electronic stethoscope 302 may be the electronic stethoscope 100 described with respect to FIGS. 1A-1C. As another example, the local computer 304 may be a cellular phone, desktop computer, laptop computer, tablet, or other electronic device capable of Bluetooth or internet connection. As a further example, the local listening device(s) 306 may be one or more electronic sound projectors, such as headphones, earbuds, hearing aids, and speakers, capable of connecting to other devices wirelessly The electronic stethoscope 302 may establish a wireless connection to the local computer 304 through a first Bluetooth connection 308. The first Bluetooth connection 308 may be a BLE connection, thereby reducing a bandwidth used for data transmission and reducing power consumption. Local computer 304 also connects to local listening device(s) 306 through a second Bluetooth connection 310. Similar to the first Bluetooth connection 308, the second Bluetooth connection 310 may be a BLE connection. Alternatively, one or both of the first Bluetooth connection 308 and the second Bluetooth connection 310 may be a regular Bluetooth connection.

The electronic stethoscope 302 may sample sound, as shown by a sampling function 312, at a desired sampling rate to produce audio data. Due to physiological sounds, such as heart and lung sounds, primarily emitting low frequency noises, the desired sampling rate may be lower than the traditional audio sampling frequency of 44 kHz. For example, the desired sampling rate may be less than 10 kHz, such as in a range between 3 kHz and 10 kHz. As one example, the desired sampling rate is 4 kHz. By sampling at 4 kHz, a data size of the audio data may be reduced, allowing for the reduced data transmission rate of the BLE links mentioned above to be used. To sample sounds, a chestpiece (e.g., the chestpiece 110 shown in FIGS. 1A and 1C) may be placed on a patient (e.g., the patient 180 shown in FIGS. 1A and 1C), and auscultation sounds may be recorded by a microphone (e.g., first microphone 162 shown in FIG. 1B) within electronic stethoscope 302 at the desired sampling rate. The electronic stethoscope 302 may perform a noise cancellation function 314 to reduce ambient noise in the audio data, such as described above with respect to FIG. 1B.

The noise-cancelled audio data is transmitted to the local computer 304 through the first Bluetooth connection 308, as shown by a first data transmission 316, and is transmitted from the local computer 304 to the local listening device(s) 306 through the second Bluetooth connection 310, as shown by a second data transmission 318. The first data transmission 316 and the second data transmission 318 may occur in substantially real-time as the audio data is generated (e.g., by the sampling function 312 and the noise cancellation function 314). As used herein, the term "real-time" refers to a process executed without intentional delay. For example, "real-time" may refer to a response time of less than or equal to about 1 second, a tenth of a second, a hundredth of a second, a millisecond, or less. In some examples, "real-time" may refer to simultaneous or substantially simultaneous audio data generation, processing, and transmission. Further, the noise cancelled audio data may be processed within an application at the local computer 304, as shown by a processing function 320, in real-time. The application may visually display a sound wave generated from the audio data so that users of the local computer 304 may be able to visually inspect and/or interpret the audio data. Additionally, the application may compare the audio data to existing audio data to suggest potential medical conditions that may be detected from the audio data.

The local listening device(s) 306 may provide additional noise cancellation, as shown by a noise cancellation function 322. For example, if local listening device(s) 306 include active noise cancellation, the local listening device(s) 306 may silence or lessen external ambient noises, such as voices, road noises, etc. In this way, quiet auscultation sounds may be heard with more clarity than if active noise cancellation is not performed at the local listening device(s) 306. The local listening device(s) 306 may project the audio data as sound, allowing for a listener of local listening device(s) 306 to hear physiological sounds of the patient, as shown by a projection function 324.

Turning now to FIG. 4, a second example communication diagram 400 is shown for data exchange between an electronic stethoscope 402, a local computer 404, an internet 403, a remote computer 405, and a remote listening device(s) 406. For example, the electronic stethoscope 402 may be the electronic stethoscope 100 described with respect to FIGS. 1A-1C. As another example, the local computer 404 may be a cellular phone, desktop computer, laptop computer, tablet, or other electronic device capable of Bluetooth or internet connection. As still another example, the remote computer 405 may be a cellular phone, desktop computer, laptop computer, and/or another computation device capable of connecting to the internet 403 and connecting to other devices wirelessly. In other examples, the remote computer 405 may be a computer network, such as a cloud computing network. Further, the remote computer 405 may be out of range of the local area around the electronic stethoscope 402 such that the remote computer 405 may not be able to connect directly to the electronic stethoscope 402, while the local computer 404 is positioned within the local area around the electronic stethoscope 402. The local area may be a physical space within a Bluetooth range around the electronic stethoscope 402, such as described with respect to the local area 230 of FIG. 2. As an example, the electronic stethoscope 402 may be located in a home of a patient (e.g., patient 180 shown in FIGS. 1A-1C) while remote computer 405 may be located miles away in a clinic. As another example, the electronic stethoscope 402 may be located in a clinic while the remote computer is in the same clinic but out of Bluetooth range of the electronic stethoscope 402. The remote listening device(s) 406 may include one or more headphones, earbuds, and/or hearing aids capable of Bluetooth or another wireless connection to other devices. Similar to the remote computer 405, the remote listening device(s) 406 are out of range for direct Bluetooth communication with the electronic stethoscope 402.

The electronic stethoscope 402 establishes a Bluetooth connection to the local computer 404 through a first Bluetooth connection 408. The local computer 404 also establishes a wireless connection to the internet 403 through a first Wi-Fi connection 409. The remote computer 405 establishes a Wi-Fi connection to the internet 403 through a second Wi-Fi connection 410. In other embodiments, the local computer 404 and the remote computer 405 may connect to the internet 403 through a wired connection, such as using an Ethernet cable. In addition to connecting to the internet 403, the remote computer 405 connects wirelessly to the remote listening device(s) 406 through a wireless connection 413. The wireless connection 413 may connect to the internet (or intranet) or a local radio network, for example, that enables the remote computer 405 to broadcast to a plurality receivers (e.g., the remote listening device(s) 406) at the same time, unlike the 1-1 communication channel functionality of Bluetooth. The remote listening device(s) 406 may be directly or indirectly connected to the remote computer 405.

The electronic stethoscope 402 samples audio via a sampling function 412 and performs noise cancellation on the sampled audio via a noise cancellation function 414, such as described above with respect to FIG. 3. The audio data is transmitted to the local computer 404 in real-time as the audio data is generated (e.g., via the sampling function 412) and processed (e.g., via the noise cancellation function 414), as shown by a first data transmission 416. The local computer 404 may send the audio data to the internet 403 in real-time through the first Wi-Fi connection 409, as shown by a second data transmission 415. The remote computer 405 may retrieve the audio data from the internet 403 in real-time, as shown by a data retrieval 417. The remote computer 405 may transmit the sampled audio data to one or more of the remote listening device(s) 406 in real-time through a third data transmission 418 using the wireless connection 413.

Active noise cancellation may be performed by the remote listening device(s) 406, as shown by a noise cancellation function 428, in order to remove or reduce the volume of external noises, as described with respect to the noise cancellation function 322 of FIG. 3. Additionally, the remote listening device(s) 406 may project the audio data as sound, as indicated by a projection function 430. In this way, the physiological sounds recorded from the patient may be "livestreamed" via the internet 403, and one or more persons not within the local range of the electronic stethoscope 402 may listen to physiological sounds in real-time. As one example, multiple listeners may listen to the livestream simultaneously, which may be particularly desirable in an educational setting where an instructor wants multiple students to listen to the same physiological sounds at the same time.

In some examples, audio data sent to the local computer 404 from the electronic stethoscope 402 may be processed in an application, as shown by a first optional processing function 420. If the local computer 404 processes the sampled data, the processed data may be sent to internet 403, shown by an optional data transmission 422 using the first Wi-Fi connection 409. The remote computer 405 may retrieve the processed data via the second Wi-Fi connection 410, as shown by an optional data retrieval 424. In other examples, the sampled data may not be processed at the local computer 404 and may instead undergo processing within the remote computer 405, as shown by a second optional processing function 426. In such examples, the first optional processing function 420 and corresponding data transmission and retrieval (e.g., the optional data transmission 422 and the optional data retrieval 424) may not occur. In other examples, processing the sampled data may occur at both the local computer 404 and the remote computer 405.

In some examples, the local computer 404 is a separate digital health device, and the audio data may help augment its capabilities. For example, the digital health device may be a digital blood pressure monitor that may use the audio data to increase accuracy via the first optional processing function 420.

Turning now to FIG. 5, a third example communication diagram 500 is shown for data exchange between an electronic stethoscope 502, an internet 504, a remote computer 506, and a remote listening device(s) 508. For example, the electronic stethoscope 502 may be the electronic stethoscope 100 shown in FIGS. 1A-1C. As another example, the remote computer 506 may be similar to the remote computer 405 described with respect to FIG. 4. As a further example, the remote listening device(s) 508 may be similar to the remote listening device(s) 406 also described with reference to FIG. 4.

The electronic stethoscope 502 may connect to the internet 504 through a first Wi-Fi connection 510. The remote computer 506 may also connect to the internet 504 through a second Wi-Fi connection 512. In other embodiments, the remote computer 506 may connect to the internet 504 using a wired connection, such as an Ethernet cable. The remote computer 506 may connect to the remote listening device(s) 508 through a Bluetooth connection 514. In other embodiments, the remote listening device(s) 508 may connect to the remote computer 506 via a wired connection, such as an auxiliary cord.

The electronic stethoscope 502 samples audio data at 4 kHz, as shown by a sampling function 516. For example, the sampling function 516 may be similar to the sampling function 312 described with respect to FIG. 3. Additionally, the electronic stethoscope 502 performs noise cancellation on the audio data, as shown by a noise cancellation function 518. The audio data is sent to the internet 504 in real-time as it is generated (e.g., via the sampling function 516 and the noise cancellation function 518) through a first data transmission 520 using the first Wi-Fi connection 510. The remote computer 506 retrieves the audio data created by the electronic stethoscope 502 in real-time through a second data transmission 522 using the second Wi-Fi connection 512. The remote computer 506 transmits the audio data generated by the electronic stethoscope 502 to the remote listening device(s) 508 in real-time through a third data transmission 524 using the Bluetooth connection 514. Thus, similar to the second communication diagram 400 of FIG. 4, the third communication diagram 500 includes livestreaming the audio data over the internet 504. However, unlike the second communication diagram 400 of FIG. 4, the electronic stethoscope 502 directly connects to the internet 504 (e.g., via the first Wi-Fi connection 510) in the third communication diagram 500, enabling the data to be transmitted with fewer intermediate (or intervening) devices.

The remote listening device(s) 508 may be capable of performing active noise cancellation, as shown by a noise cancellation function 528. A projection function 530 shows the remote listening device(s) projecting sound based on the audio data created by the electronic stethoscope 502. There may be one or more listeners to the audio data depending on the type of listening device and a number of listening devices connected to the remote computer 506.

Additionally, the remote computer 506 may process the audio data in an application using a processing function 526. Similar to the processing function 320 shown in FIG. 3, the audio data may be visually displayed via a display device using the application. As another example, the application may analyze a waveform of the audio data, for example.

Figure 6:
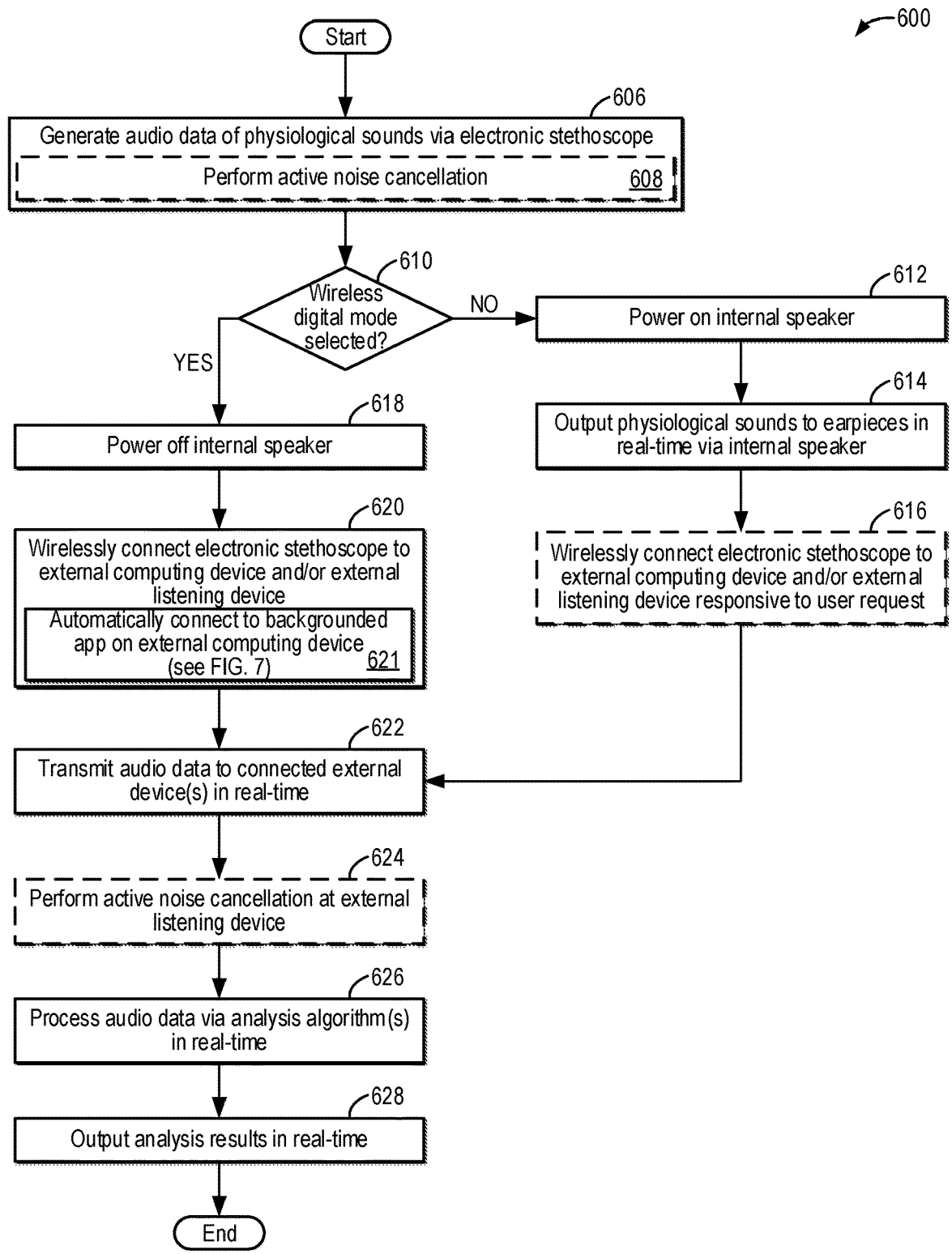
FIG. 6 is a method for operating an electronic stethoscope to generate audio data and wireless transmitting the audio data to one or more external devices.

Turning now to FIG. 6, a method 600 is shown for operating an electronic stethoscope in a digital mode to record physiological sounds from a patient (or subject) and transmit audio data of the physiological sounds to other, connected devices. For example, the electronic stethoscope may be the electronic stethoscope 100 shown in FIGS. 1A-1C. As another example, the digital mode may be active when a switch (e.g., switching valve 146 shown in FIG. 1B) is closed, thereby enabling power to be supplied to electrical components within the electronic stethoscope. Further, the electronic stethoscope may be operated in two different digital modes depending on whether or not earpieces of the electronic stethoscope are physically connected to an output of the electronic stethoscope. For example, the digital mode may have two sub-modes, one of the sub-modes (e.g., a first, wired digital mode) including operating with an internal speaker of the electronic stethoscope active and the other of the sub-modes (e.g., a second, wireless digital mode) including operating with the internal speaker of the electronic stethoscope deactivated. Thus, an operation (e.g., an operating mode) of the electronic stethoscope may be changed based on a detected user action, such as the user changing the mechanical configuration at the output by disconnecting the earpieces or inputting a mode selection. Instructions for carrying out the method 600 and the rest of the methods included herein may be executed by one or more processors, including a CPU of the electronic stethoscope (e.g., CPU 151 of FIG. 1B) based on instructions stored on a memory operatively coupled to each of the one or more processors (e.g., the memory 153 of FIG. 1B) and in conjunction with signals received from electronic components of the electronic stethoscope.

At 606, the method 600 includes generating audio data of the physiological sounds via the electronic stethoscope. The physiological sounds may be heart sounds, lung sounds, bowel sounds, fistula sounds, or any other measurable sound made by the patient's body. In order to generate the audio data of the physiological sounds, the electronic stethoscope may be placed on the patient (e.g., the patient 180 shown in FIGS. 1A and 1C), and a microphone (e.g., the first microphone 162 shown in FIG. 1B) may convert the physiological sounds into an electronic signal. For example, the electronic stethoscope, specifically a chestpiece of the electronic stethoscope (e.g., the chestpiece 110 shown in FIGS. 1A and 1C), may be placed on the patient by the patient or by a clinician, and the chestpiece may transmit and amplify vibrations from the physiological sounds to the microphone. As a further example, the clinician may directly hold the electronic stethoscope to place the electronic stethoscope on the patient, or the electronic stethoscope may be attached to a dedicated holder (e.g., rod), and the clinician may place the electronic stethoscope onto the patient via the holder while maintaining a greater distance from the patient than when the dedicated holder is not used. By the patient placing the electronic stethoscope or the clinician using the dedicated holder, contact between the clinician and the patient may be reduced, such as in circumstances of infectious diseases.

Generating the audio data optionally includes performing active noise cancellation, as indicated at 608. The electronic stethoscope may include a second microphone (e.g., the second microphone 164 shown in FIG. 1B), which may record ambient noise from an environment around the electronic stethoscope and generate an electronic noise signal. An electronic acoustic modifier (e.g., the electronic acoustic modifier 154 shown in FIG. 1B) may receive the electronic noise signal from the second microphone and use the electronic noise signal to reduce or eliminate the ambient noise from the audio data of the physiological sounds.

At 610, the method 600 includes determining if the wireless digital mode is selected. The wireless digital mode may be selected based on a detected action performed by (or an input received from) a user, for example. As one example, it may be determined that the wireless digital mode is selected when the user disconnects the earpieces (e.g., the earpieces 116 shown in FIG. 1A) from the electric stethoscope device. For example, the electronic stethoscope device may actively detect whether or not the earpieces are mechanically, acoustically, and/or electronically connected based on electronic feedback received from a switch (e.g., the switch 148 of FIG. 1B) or another input received from a user, sensor, or other electronic component (e.g., the speakers 117). Additional details regarding determining whether or not the earpieces are connected are described above with respect to FIG. 1B. As another example, the wireless digital mode may be selected in response to input received via a user interface, such as a user interface of the electronic stethoscope (e.g., the mode selection input 160 shown in FIGS. 1A-1C) or a user interface of an external computing device (e.g., the user interface 168 shown in FIGS. 1A and 1C). For example, the user may select the wireless digital mode by changing a position of a button or switch on the electronic stethoscope. As another example, the user may select the wireless digital mode via a software application (e.g., app) operating on the external computing device, and the external computing device may connect to and wirelessly transmit the selection to the electronic stethoscope device, as will be elaborated below.

If the wireless digital mode is not selected during digital operation of the electronic stethoscope, then the wired digital mode is selected. The wired digital mode includes using components that are entirely internal to (e.g., part of) the electronic stethoscope to project sound. Therefore, the wired digital mode is also referred to herein as an internal digital mode. For example, the internal digital mode may include acoustically transmitting sound via the internal speaker. The internal speaker may be the speaker 174 shown in FIG. 1B that is internal to the body of the electronic stethoscope device or the speakers 117 shown in FIG. 1A that are internal to the earpieces of the electronic stethoscope. As such, the internal speaker may include a direct or indirect wired connection with audio recording and processing components of the electronic stethoscope device. Alternatively, the internal speaker may use another form of internal communication with the audio recording and processing components. In contrast, the wireless digital mode is an external digital mode that includes exclusively using components that are external to (e.g., not part of) the electronic stethoscope to project sound.

In some examples, the wired digital mode may be automatically selected when the wireless digital mode is not selected. Additionally or alternatively, the wired digital mode may be selected based on the detected action performed by (or input received from) the user. As one example, it may be determined that the wired digital mode is selected when the user mechanically and acoustically connects the earpieces to the electric stethoscope device, which may be detected based on the electronic feedback received from the switch, sensor, or other electronic component. As another example, the wired digital mode may be selected in response to input received via the user interface of the electronic stethoscope or the external computing device. For example, the user may select the wired digital mode via the app operating on the external computing device, and the external computing device may wirelessly transmit the selection to the electronic stethoscope device.

If the wireless digital mode is not selected (e.g., the wired digital mode is selected), the method 600 proceeds to 612 and includes powering on (e.g., activating) the internal speaker (or speakers). Alternatively, if the internal speaker is already powered on, the method 600 may include maintaining the internal speaker powered on. Thus, when the wired digital mode is selected, the electronic stethoscope is operated in the first, wired digital mode, with the internal speaker activated.

At 614, the method 600 includes outputting the physiological sounds to the earpieces of the electronic stethoscope through the internal speaker. As such, while operating in the wired digital mode, the physiological sounds are projected by the internal speaker and delivered via the earpieces of the electronic stethoscope.

At 616, the method 600 optionally includes wirelessly connecting the electronic stethoscope to an external computing device and/or an external listening device. The external computing device may be a local device (e.g., within a defined range around the electronic stethoscope that enables short-range wireless connections) or a remote device (e.g., outside of the defined range around the electronic stethoscope), such as described above with respect to FIGS. 2-5. For example, the external computing device may be a desktop or laptop computer, a cellular phone (smartphone), a tablet, a wearable device (e.g., a smartwatch), a digital (e.g., electronic) health monitoring device, or other computing device having a wireless receiver/transceiver. The electronic stethoscope may connect to the external computing device through a short-range wireless connection, such as Bluetooth (e.g., BLE), or may use a longer-range wireless connection (e.g., Wi-Fi), particularly if the external computing device is remote. In some examples, the electronic stethoscope may connect to more than one external computing device. Connecting to the external computing device(s) may enable the physiological sounds to be analyzed, saved, and/or livestreamed in order to reach a plurality of listeners.

For example, as described with particular respect to FIG. 3, the electronic stethoscope may establish a direct BLE connection with the external computing device when the external computing device is local in response to input received via the software application running on the external computing device. As another example, the electronic stethoscope may establish a direct BLE connection to a first external computing device, and the first external computing device may further connect the electronic stethoscope to a second external computing device via the internet, such as described with respect to FIG. 4. As still another example elaborated above with respect to FIG. 5, the electronic stethoscope may connect to the internet, and the electronic stethoscope may connect to one or more external computing devices via the internet, particularly when the external computing device is remote.

As another example, the electronic stethoscope may connect to the external listening device in addition to maintaining the internal speaker (or speakers) active and powered on, at least in some examples. The external listening device may be a pair of headphones or earbuds, a hearing aid, a speaker, or another device with wireless connection and sound projection capabilities. As one example, the electronic stethoscope may directly connect to the external listening device, such as via Bluetooth (e.g., BLE or LE Audio), when the external listening device is local to the electronic stethoscope, such as in response to input received via the app running on the external computing device. For example, the electronic stethoscope may connect to the external computing device via a first Bluetooth radio (e.g., transceiver) and may connect to the external listening device via a second Bluetooth radio. Direct connection to a local listening device is further described above with respect to FIG. 2. As another example, the electronic stethoscope may connect to the external listening device through the established connection with the external computing device. In some examples, the external listening device may be part of the external computing device. For example, the external listening device may be a computer speaker. In other examples, the external computing device may wirelessly connect to the external listening device (e.g., via BLE or LE Audio) or may have a wired connection with the external listening device (e.g., via an auxiliary cord), such as described with respect to FIGS. 2-5. Further, the external computing device may facilitate the transmission of data from the electronic stethoscope to the external listening device via the software application, even while the application is running in the background. This minimizes power consumption on the external computing device and provides a more favorable user experience. Further, in some examples, the electronic stethoscope may connect to more than one external listening device. For example, the electronic stethoscope may indirectly connect to a plurality of external listening devices by connecting to a broadcasting device.

In some examples, the first Bluetooth transceiver and/or the second Bluetooth transceiver may remain powered off, even while the electronic stethoscope device is powered on, when the wired digital mode is selected unless otherwise requested via user input. As such, while operating in the wired digital mode, the first Bluetooth transceiver and/or the second Bluetooth transceiver may be powered on in response to a user request to connect to the external computing device and/or the external listening device. By maintaining the first Bluetooth transceiver and/or the second Bluetooth transceiver powered off when wireless communication is not desired, power consumption by the electronic stethoscope device may be reduced.

Returning to 610, if the wireless digital mode is selected, the method 600 proceeds to 618 and includes powering off (e.g., deactivating) the internal speaker. Alternatively, if the internal speaker is already shut off, the internal speaker may be maintained powered off. By powering off the internal speaker, power consumption is reduced, which may increase a battery life of the electronic stethoscope device. Further, the projection of unwanted sounds to the ambient environment is prevented, which increases user satisfaction. Thus, the electronic stethoscope is operated in the wireless digital mode, with the internal speaker deactivated, when the wireless digital mode is selected and/or when the wired digital mode is not selected.

At 620, the method 600 includes wirelessly connecting the electronic stethoscope to the external computing device and/or the external listening device, similar to that described above at 616. Thus, while wirelessly connecting the electronic stethoscope to the external listening device is optional while operating in the wired digital mode, wirelessly connecting the electronic stethoscope to the external computing device and/or the external listening device may be performed automatically while operating in the wireless digital mode. For example, the electronic stethoscope may turn on the second Bluetooth radio responsive to the earpieces being disconnected without additional input from the user. Additionally or alternatively, the electronic stethoscope may automatically turn on the second Bluetooth radio responsive to the wireless digital mode being selected via the input to the user interface.

In particular, the electronic stethoscope may automatically connect to the software application running on the external computing device in the background mode, as indicated at 621. As will be elaborated below with respect to FIG. 7, the electronic stethoscope may utilize a previously received permission to connect to the external computing device without receiving additional input from the user via the software application at the time of connection. For example, the electronic stethoscope may establish the wireless connection in response to the wireless digital mode being selected.

At 622, the method 600 includes transmitting the audio data to the connected external device(s) in real-time. The electronic stethoscope may use the wireless connection to transmit the audio data to the external device(s), such as the external computing device (e.g., if connected at 616 or as connected at 620) and the external listening device (e.g., if connected at 616 or as connected 620), as the data is generated and without intentional delay. In this way, listeners who are not using the earpieces of the electronic stethoscope may be able to hear the recorded auscultations in real-time.

At 624, the method 600 optionally includes performing active noise cancellation at the external listening device. The external listening device may be configured to reduce or eliminate ambient sounds from the environment in which the external listening device is positioned, which may be different than the ambient noise of the electronic stethoscope. In such examples, the external listening device itself may reduce or prevent the ambient sounds from being heard through the external listening device. As such, the physiological sounds may be heard with greater clarity. In other examples, such as when the external listening device does not include active noise cancellation, 624 may be omitted.

At 626, the method 600 includes processing the audio data via at least one analysis algorithm in real-time. The at least one analysis algorithm may be trained to detect one or more disease states or conditions, such a heart murmur or other heart sound, as well as physiological parameters, such as heart rate or other metrics. The heart murmur may be a systolic murmur or a diastolic murmur. Further, the systolic murmur may be caused by an aortic stenosis, a pulmonic stenosis, a mitral regurgitation, a tricuspid regurgitation, a mitral valve prolapse, or another condition. The diastolic murmur may be caused by an aortic regurgitation, a pulmonic regurgitation, a mitral stenosis, a tricuspid stenosis, or another condition. In some examples, the trained algorithm may process the audio data on the external computing device, the electronic stethoscope device, or both. Additionally or alternatively, the algorithm may process the data in a cloud system, such as a distributed cloud computer system.

Further, in some examples, the user may trigger data analysis, annotations, and/or recordings by inputting commands via the user interface, such as via the software application. For example, the user may input the commands in real-time or in less than real-time, such as to further evaluate previously recorded physiological sounds.

At 628, the method includes outputting the analysis results in real-time. The analysis results may be an output of the at least one analysis algorithm and may be visually output and/or audibly output. For example, the analysis results may be output to a display of the user interface as a written message. Additionally or alternatively, the analysis results may be output via the external listening device(s), when connected, and/or the internal speaker, when powered on, as an audio message. As an example, the message may state, "Systolic murmur detected" when the analysis algorithm identifies a systolic murmur. Further still, the analysis results may be output to a report within the software application, which may be automatically saved even when the application is running in the background mode. The method 600 may then end.

Figure 7:
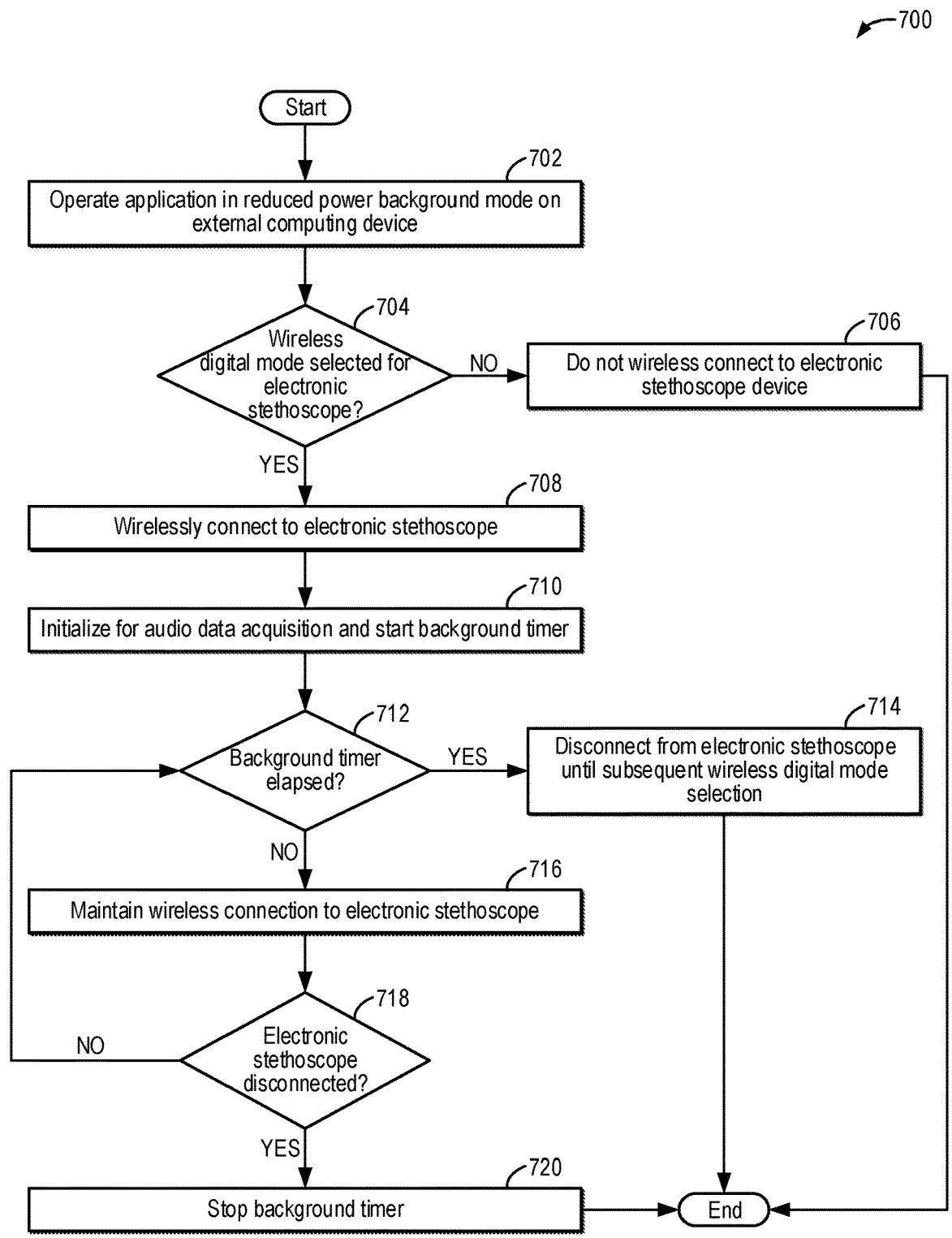
FIG. 7 is a method for automatically connecting an external computing device to an electronic stethoscope when a wireless mode is initiated.

Referring now to FIG. 7, a method 700 for establishing an automatic wireless connection between an electronic stethoscope and an external computing device (e.g., external to the electronic stethoscope) is shown. Instructions for carrying out the method 700 may be executed by one or more processors, including a processor of the electronic stethoscope (e.g., the CPU 151 of FIG. 1B) and a processor of the external computing device (e.g., the external computing device 184 shown in FIGS. 1A and 1C) based on instructions stored on a memory operatively coupled to each of the one or more processors (e.g., the memory 153 of FIG. 1B) and in conjunction with signals received from electronic components of the electronic stethoscope and the external computing device. In some examples, the method 700 may be performed as a part of or in parallel to the method 600 of FIG. 6.

At 702, the method 700 includes operating a software application in a reduced power background mode on the external computing device. For example, the external computing device may be a desktop or laptop computer, a cellular phone (smartphone), a tablet, a wearable device (e.g., a smartwatch), a digital (e.g., electronic) health monitoring device, or other computing device having a wireless receiver/transceiver, particularly a Bluetooth receiver/transceiver. The software application may be a companion application to the electronic stethoscope that enables a user to interface with the electronic stethoscope wirelessly from the external computing device. For example, the user may provide inputs that give the software application permission to connect to the electronic stethoscope while in the background mode and may further adjust settings for the connection via a user interface of the external computing device (e.g., the user interface 168 shown in FIGS. 1A and 1C) while the software application is launched and running in a non-backgrounded, full power mode. For example, the app may be displayed on a display screen of the user interface while the application is launched, whereas the app may not be displayed on the display screen while the application is running in the background mode. As another example, the application may receive user inputs while launched, and the application may not receive user inputs while in the background mode.

After setting up the permission, the user may place the software application in the background mode via a pre-programmed input. Alternatively, the software application may "time out" and automatically place itself into the background mode when no input has been received for at least a pre-programmed threshold duration while the application is running in the full-power mode. The pre-programmed threshold duration may be a non-zero time value stored in the memory that is calibrated to reduce power consumption while minimizing unwanted backgrounding of the app, which may disrupt a workflow of the user.

At 704, the method 700 includes determining if a wireless digital mode is selected for the electronic stethoscope. The wireless digital mode may be selected as described above with respect to 610 of FIG. 6. As one example, the software application may determine that the wireless digital mode is selected based on a signal received from a Bluetooth transceiver of the electronic stethoscope. As another example, the software application may determine that the wireless digital mode is not selected when the signal is not received from the Bluetooth transceiver. Alternatively, a different signal may indicate that the wireless digital mode is not selected (e.g., a wired digital mode is selected).

If the wireless digital mode is not selected for the electronic stethoscope, such as when the wired digital mode is selected or the electronic stethoscope is powered off, the method 700 proceeds to 706 and includes not wirelessly connecting to the electronic stethoscope device. As such, power consumption on the external computing device by the software application may be reduced. The method 700 may then end.

Returning to 704, if the wireless digital mode is selected for the electronic stethoscope, the method 700 proceeds to 708 and includes wirelessly connecting to the electronic stethoscope. With the software application running in the background mode and the wireless digital mode selected, the external computing device may automatically connect to the electronic stethoscope using the previously received permission and without additional input from the user at the time of the connection. For example, the external computing device may connect to the electronic stethoscope as soon as the signal is received from the Bluetooth transceiver of the electronic stethoscope.

At 710, the method 700 includes initializing the software application for audio data acquisition and starting a background timer. The background timer may be a pre-programmed time duration that may be adjusted by the user, allowing the user to customize the amount of time that the external computing device remains connected to the electronic stethoscope while the app is running in the background mode. For example, the background timer may count up from zero to the pre-programmed time duration. As another example, the background timer may count down from the pre-programmed time duration to zero. Further, by initializing the software application for audio data application, the external computing device may be prepared to receive audio data from the electronic stethoscope, which may be analyzed, recorded, and/or streamed to listening device(s) by the software application while the software application remains in the background mode.

At 712, the method 700 includes determining if the background timer has elapsed. For example, the background timer has elapsed after the pre-programmed duration has elapsed since the timer was started. When counting up, the background timer is considered to be elapsed when the background timer reaches the pre-programmed time duration. When counting down, the background timer is considered to be elapsed when the background timer reaches zero. In contrast, the background timer has not elapsed when a time value is between zero and the pre-programmed duration.

If the background timer has elapsed, the method 700 proceeds to 714 and includes disconnecting the external computing device from the electronic stethoscope until a subsequent wireless digital mode selection. With the electronic stethoscope disconnected, the external computing device will no longer receive audio data from the electronic stethoscope, and power consumption on both the electronic stethoscope and the external computing device may be reduced. The method 700 may then end.

Returning to 712, if the background timer has not elapsed, the method 700 proceeds to 716 and includes maintaining the wireless connection to the electronic stethoscope. As such, the external computing device may continue to receive audio data from the electronic stethoscope as it is recorded, which may be analyzed, stored, and/or streamed to a listener from the software application while the application remains in the background mode.

At 718, the method 700 includes determining if the electronic stethoscope has been disconnected. It may be determined that the electronic stethoscope has been disconnected when the external computing device no longer receives the signal from the electronic stethoscope transceiver, for example. As an example, the electronic stethoscope may be disconnected by the user powering off the electronic stethoscope or switching off the wireless digital mode.

At 720, the method 700 includes stopping the background timer. With the electronic stethoscope disconnected, the background timer may be reset so that it may be restarted with the full pre-programmed duration upon a subsequent connection with the electronic stethoscope to operate in the wireless digital mode while the software application is running in the background. The method 700 then ends.

In this way, the electronic stethoscope may be used to record physiological sounds from a patient and wirelessly transmit audio data of the physiological sounds to one or more other electronic devices in real-time, as the physiological sounds occur. For example, the electronic stethoscope may transmit the audio data via Bluetooth (e.g., BLE) and/or Wi-Fi. Because the connectivity of the electronic stethoscope enables real-time audio data streaming to one or a plurality of external computing and/or listening devices, a plurality of listeners and/or applications may receive the audio data at the same time for listening or further processing, even while an application on the external computing device(s) receiving the audio data is in a background mode. Additionally, the plurality of listeners and/or applications may be remote from each other as well as remote from the device. Overall, the audio data may be shared more efficiently, which may help reduce a time until a patient diagnosis is made as well as increase learning opportunities in educational settings.

The technical effect of adjusting a state of an internal speaker of an electronic stethoscope based on a change in a mechanical configuration of the electronic stethoscope or an external input from a connected computing device is that the electronic stethoscope may be efficiently operated in a remote patient monitoring mode.

The disclosure also provides support for a method, comprising: operating an electronic stethoscope in one of an internal digital mode and a wireless digital mode based on a detected user action. In a first example of the method, the detected user action is received via a user interface. In a second example of the method, optionally including the first example, the user interface is one of a button, a switch, and a toggle positioned on a body of the electronic stethoscope. In a third example of the method, optionally including one or both of the first and second examples, the user interface is included in a computing device wirelessly communicating with the electronic stethoscope, and wherein the detected user action is input into a software application running on the computing device. In a fourth example of the method, optionally including one or more or each of the first through third examples, the method further comprises: wirelessly transmitting data from the electronic stethoscope to the computing device while operating the electronic stethoscope in the wireless digital mode, and further transmitting the data from the computing device to at least one listening device in electronic or wireless communication with the computing device. In a fifth example of the method, optionally including one or more or each of the first through fourth examples, the software application running on the computing device is running in a background mode on the computing device, and wherein the software application receives the data from the electronic stethoscope and transmits the data to the at least one listening device while running in the background mode. In a sixth example of the method, optionally including one or more or each of the first through fifth examples, operating the electronic stethoscope in the internal digital mode comprises powering speakers electrically connected to the electronic stethoscope, and wherein operating the electronic stethoscope in the wireless digital mode comprises not powering the speakers electrically connected to the electronic stethoscope. In a seventh example of the method, optionally including one or more or each of the first through sixth examples, operating the electronic stethoscope in the wireless digital mode comprises: generating audio data, and wirelessly transmitting the generated audio data to at least one external device in real-time. In an eighth example of the method, optionally including one or more or each of the first through seventh examples, the at least one external device comprises one or more of a laptop computer, a smartphone, a tablet, headphones, earbuds, and a speaker that is not physically or electrically connected to the electronic stethoscope, and the method further comprises: analyzing the audio data via an analysis algorithm, and outputting analysis results from the analysis algorithm to the at least one external device. In a ninth example of the method, optionally including one or more or each of the first through eighth examples, the detected user action is a mechanical configuration change of an output of the electronic stethoscope. In a tenth example of the method, optionally including one or more or each of the first through ninth examples, the mechanical configuration change of the output of the electronic stethoscope is a mechanical and acoustic disconnection of earpieces of the electronic stethoscope from a body of the electronic stethoscope at the output, and the method further comprises operating the electronic stethoscope in the wireless digital mode in response to the mechanical and acoustic disconnection of the earpieces. In an eleventh example of the method, optionally including one or more or each of the first through tenth examples, the mechanical configuration change of the output of the electronic stethoscope is a mechanical and acoustic connection of earpieces of the electronic stethoscope to a body of the electronic stethoscope at the output, and the method further comprises operating the electronic stethoscope in the internal digital mode in response to the mechanical and acoustic connection of the earpieces.

The disclosure also provides support for a method for an electronic stethoscope, comprising: changing a mode of operation of the electronic stethoscope between an internal digital mode that comprises operating with an internal speaker of the electronic stethoscope powered on and a wireless digital mode that comprises operating with the internal speaker of the electronic stethoscope powered off in response to a detected user action. In a first example of the method, the detected user action is a mechanical and acoustic disconnection of earpieces of the electronic stethoscope from a body of the electronic stethoscope, and wherein changing the mode of operation between the internal digital mode and the wireless digital mode comprises changing the mode of operation to the wireless digital mode in response to the mechanical and acoustic disconnection of the earpieces of the electronic stethoscope from the body of the electronic stethoscope. In a second example of the method, optionally including the first example, the method further comprises: in response to the mechanical and acoustic disconnection of the earpieces of the electronic stethoscope from the body of the electronic stethoscope: activating a wireless transceiver of the electronic stethoscope, and establishing a wireless connection between the electronic stethoscope and an external listening device via the wireless transceiver. In a third example of the method, optionally including one or both of the first and second examples, the method further comprises: generating audio data of physiological sounds via the electronic stethoscope, wirelessly transmitting the audio data to the external listening device in real-time during the generating via the wireless connection, analyzing the audio data in real-time during the generating via one or more trained algorithms, and wirelessly transmitting an analysis result of the one or more trained algorithms to the external listening device in real-time. In a fourth example of the method, optionally including one or more or each of the first through third examples, the detected user action is a mechanical and acoustic connection of earpieces of the electronic stethoscope to a body of the electronic stethoscope, and wherein changing the mode of operation between the internal digital mode and the wireless digital mode comprises changing the mode of operation to the internal digital mode in response to the mechanical and acoustic connection of the earpieces of the electronic stethoscope to the body of the electronic stethoscope.

The disclosure also provides support for a system for an electronic stethoscope device, comprising: a body configured to be removably coupled to earpieces at an output of the body, and a control and processing unit (CPU) operatively coupled to a memory storing instructions that, when executed by the CPU, cause the CPU to: select a digital operating mode of the electronic stethoscope device based on whether or not the earpieces are coupled to the output of the body. In a first example of the system, the system further comprises: a switch positioned at the output of the body of the electronic stethoscope device, the switch configured to be in an open position when the earpieces are connected to the output of the body and configured to be in a closed position when the earpieces are not coupled to the output of the body, and wherein to select the digital operating mode of the electronic stethoscope device based on whether or not the earpieces are coupled to the output of the body, the instructions, when executed, cause the CPU to: select an internal digital operating mode when a detected position of the switch is the open position, and select a wireless digital operating mode when the detected position of the switch is the closed position. In a second example of the system, optionally including the first example, the system further comprises: a plurality of wireless transceivers internal to the body of the electronic stethoscope device, and wherein the memory stores further instructions that, when executed by the CPU, cause the CPU to: establish a wireless connection between at least one of the plurality of wireless transceivers and an external electronic device when the detected position of the switch is the closed position.

Certain adaptations and modifications of the described embodiments can be made. Therefore, the above discussed embodiments are considered to be illustrative and not restrictive. The present disclosure is not to be limited in scope by the specific embodiments described herein. Further example embodiments may also include all of the steps, features, and components referred to or indicated in this description, individually or collectively and any and all combinations or any two or more of the steps or features.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method, comprising:
   operating an electronic stethoscope device in one of an internal digital mode and a wireless digital mode based on a detected user action, wherein:
      operating the electronic stethoscope device in the internal digital mode comprises powering speakers electrically connected to the electronic stethoscope device; and
      operating the electronic stethoscope device in the wireless digital mode comprises not powering the speakers electrically connected to the electronic stethoscope device, generating audio data, and wirelessly transmitting the generated audio data to at least one external device in real-time, the at least one external device configured to wirelessly capture or play the generated audio data in real-time via at least one listening device that is not physically or electronically connected to the electronic stethoscope device, wherein the detected user action is a mechanical configuration change of an output of the electronic stethoscope device, and wherein the mechanical configuration change of the output of the electronic stethoscope device is a mechanical and acoustic disconnection of earpieces of the electronic stethoscope device from a body of the electronic stethoscope device at the output;
   operating in the internal digital mode, including powering the speakers electrically connected to the electronic stethoscope device and playing first audio data via the speakers electrically connected to the electronic stethoscope device;
   in response to the mechanical and acoustic disconnection of the earpieces, automatically covering and sealing the output via a spring-loaded cap and switching from operating in the internal digital mode to operating the electronic stethoscope device in the wireless digital mode, wherein switching from operating the electronic stethoscope device in the internal digital mode to operating the electronic stethoscope device in the wireless digital mode comprises powering off the speakers electrically connected to the electronic stethoscope device in response to the mechanical and acoustic disconnection of the earpieces, generating the audio data via a microphone of the electronic stethoscope device, and initiating the wirelessly transmitting of the generated audio data to the at least one external device in real-time; and
   playing the generated audio data at the at least one listening device that is not physically or electronically connected to the electronic stethoscope device.

2. The method of claim 1, wherein the detected user action is received via a user interface.

3. The method of claim 2, wherein the user interface is one of a button, a switch, and a toggle positioned on the body of the electronic stethoscope device.

4. The method of claim 2, wherein the at least one external device includes a computing device, wherein the user interface is included in the computing device, and wherein the detected user action is input into a software application running on the computing device.

5. The method of claim 4, further comprising:
   wirelessly transmitting the generated audio data from the electronic stethoscope device to the computing device while operating the electronic stethoscope device in the wireless digital mode; and
   further transmitting the data from the computing device to at least one listening device in electronic or wireless communication with the computing device.

6. The method of claim 4, wherein the software application running on the computing device is running in a background mode on the computing device, and wherein the software application receives the generated audio data from the electronic stethoscope device and transmits the generated audio data to the at least one listening device while running in the background mode.

7. The method of claim 1, wherein the at least one external device comprises one or more of a laptop computer, a smartphone, a tablet, headphones, and earbuds, and the method further comprises:
   analyzing the audio data via an analysis algorithm; and
   outputting analysis results from the analysis algorithm to the at least one external device.

8. The method of claim 1, further comprising operating the electronic stethoscope device in the internal digital mode in response to a mechanical and acoustic connection of the earpieces.

9. The method of claim 1, further comprising detecting the mechanical and acoustic disconnection of the earpieces of the electronic stethoscope device from the body of the electronic stethoscope device based on at least one of:
   signals analyzed from the microphone of the electronic stethoscope device; and
   a distance of the earpieces from the electronic stethoscope device measured by a proximity sensor.

10. The method of claim 1, further comprising operating the electronic stethoscope device in the wireless digital mode in response to the mechanical and acoustic disconnection of the earpieces, and wirelessly playing the generated audio data in real-time at the least one listening device, wherein sound is no longer transmitted at the speaker.

* * * * *